United States Patent
Mei et al.

(10) Patent No.: US 8,461,114 B2
(45) Date of Patent: Jun. 11, 2013

(54) METHODS AND COMPOSITIONS FOR MODULATING ERBB2 ACTIVITY

(75) Inventors: Lin Mei, Evans, GA (US); Yanmei Tao, Martinez, GA (US); Wen-Chen Xiong, Evans, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 327 days.

(21) Appl. No.: 12/780,065

(22) Filed: May 14, 2010

(65) Prior Publication Data

US 2010/0291077 A1    Nov. 18, 2010

Related U.S. Application Data

(60) Provisional application No. 61/216,218, filed on May 14, 2009.

(51) Int. Cl.
*A61K 38/00* (2006.01)

(52) U.S. Cl.
USPC .......................................... 514/12; 530/300

(58) Field of Classification Search
None
See application file for complete search history.

(56) References Cited

U.S. PATENT DOCUMENTS

2004/0014055 A1*  1/2004  Birnbaum et al. ................. 435/6

OTHER PUBLICATIONS

Borg et al. (Nature Cell Biology, vol. 2, pp. 407-414, Jul. 2000) of record.*
Adlkofer and Lai, "Role of neuregulins in glial cell development", Glia, 29:104-11 (2000).
Borg, et al., "ERBIN: A basolateral PDZ protein that interacts with the mammalian ERBB2/HER2 receptor", Nat. Cell Biol., 2:407-414 (2000).
Chen, et al., "Disruption of ErbB receptor signaling in adult non-myelinating Schwann cells causes progressive sensory loss", Nat Neurosci., 6:1186-1193 (2003).
Chen, et al., "Neuregulin 1-erbB signaling is necessary for normal myelination and sensory function", J. Neurosci., 26:3079-3086 (2006).
Dai, et al. "Erbin inhibits transforming growth factor beta signaling through a novel Smad-interacting domain", Mol. Cell Biol., 27:6183-6194 (2007).
Dai, et al., "Erbin inhibits RAF activation by disrupting the sur-8-Ras-Raf complex", J. Biol. Chem., 281:927-933 (2006).
Dardousis, et al., "Identification of differentially expressed genes involved in the formation of multicellular tumor spheroids by HT-29 colon carcinoma cells", Molecular Therapy, 15(1):94-102 (2007).
Favre, et al., "The hemidesmosomal protein bullous pemphigoid antigen 1 and the integrin beta 4 subunit bind to ERBIN. Molecular cloning of multiple alternative splice variants of ERBIN and analysis of their tissue expression", J. Biol. Chem., 276:32427-32436 (2001.
Flores, et al., "Constitutively active Akt induces enhanced myelination in the CNS", J. Neurosci., 8:7174-7183 (2008).
Garratt, et al., "A dual role of erbB2 in myelination and in expansion of the schwann cell precursor pool", J. Cell Biol., 148:1035-1046 (2000).
Gatto, et al., "Asymmetric ERM activation at the Schwann cell process tip is required in axon-associated motility", J. Cell Physiol., 210:122-132 (2007).
Guy, et al., "Insect cell-expressed p180erbB3 possesses an impaired tyrosine kinase activity", Proc. Natl. Acad. Sci. USA., 91:8132-8136 (1994).
Haastert, et al., "Human and rat adult Schwann cell cultures: Fast and efficient enrichment and highly effective non-viral transfection protocol", Nat. Proto., 2:9-104 (2007).
Holmes, et al., "Identification of heregulin, a specific activator of p185erbB2", Science, 256:1205-10 (1992).
Hsieh, et al., "ERbB-2 expression is rate-limiting for epidermal growth factor-mediated stimulation of ovarian cancer cell proliferation", Intl. J. of Cancer, 86:644-651 (2000).
Huang, et al., "Erbin is a protein concentrated at postsynaptic membranes that interacts with PSD-95", J. Biol. Chem., 276:19318-26 (2001).
Huang, et al., "Erbin suppresses the MAP kinase pathway", J. Biol. Chem., 278:1108-1114 (2003).
Kim, et al., "The role of ErbB2 signaling in the onset of terminal differentiation of oligodendrocytes in vivo", J. Neurosci., 23:5561-5571 (2003).
Kim, et al., "Quercetin decreases the expression of ErbB2 and ErbB3 proteins in HT-29 human colon cancer cells", J. Nutritional Biochemistry, 16:155-162 (2005).
Kolch, "Erbin: Sorting out ErbB2 receptors or giving Ras a break?", Sci. STKE., (199):pe37, (2003).
Laura, et al., "The Erbin PDZ domain binds with high affinity and specificity to the carboxyl termini of delta-catenin and ARVCF", J. Biol. Chem., 277:12906-12914 (2002).
Lee, et al., "Requirement for neuregulin receptor erbB2 in neural and cardiac development", Nature, 378:394-398 (1995).
Liu, et al., "Erbin-regulated sensitivity of MCF-7 breast cancer cells to TRAIL via ErbB2/AKT/NF-kappaB pathway", J. of Biochemistry, 143(6)793-801 (2008).
McDonald, et al., "A role for Erbin in the regulation of Nod2-dependent NF-kappaB signaling", J. Biol. Chem., 280:40301-40309 (2005).
Mei and Xiong, "Neuregulin 1 in neural development, synaptic plasticity and schizophrenia", Nat. Rev. Neurosci., 9:437-452 (2008).
Meyer and Birchmeier, "Multiple essential functions of neuregulin in development", Nature, 378:386-390 (1995).

(Continued)

*Primary Examiner* — Laura B Goddard
*Assistant Examiner* — Meera Natarajan
(74) *Attorney, Agent, or Firm* — Pabst Patent Group LLP

(57) ABSTRACT

Modulating the interaction between ErbB2 and Erbin is an effective method for treating one or more symptoms of ErbB2-mediated disorders. It has been discovered that Erbin stabilizes ErbB2 in vivo and inhibiting the formation of heterodimers between Erbin and ErbB2 reduces or inhibits the biological activity of ErbB2 relative to control levels. Reducing the biological activity of ErbB2 is useful in the treatment of conditions characterized by the overexpression or misregulation of ErbB2. These conditions include, but are not limited to breast cancer and prostate cancer. Alternatively, agonist of Erbin that promote or enhance the interaction of Erbin with ErbB2 can be useful in the treatment of certain neurological disorders. It has also been discovered that Erbin plays a role in the myelination of neurons of the peripheral nervous system.

6 Claims, 20 Drawing Sheets

OTHER PUBLICATIONS

Michailov, et al., "Axonal neuregulin-1 regulates myelin sheath thickness", Science, 2004;304:700-703 (2004).

Negro, A, et al., "Essential roles of Her2/erbB2 in cardiac development and function", Recent Progress in Hormone Research, 59:1-12 (2004).

Perrin-Tricaud, et al., "P120 catenin is required for thickening of Schwann cell myelin", Mol Cell Neurosci., 35:120-129 (2007).

Rangwala, et al., "Erbin regulates mitogen-activated protein (MAP) kinase activation and MAP kinase-dependent interactions between Merlin and adherens junction protein complexes in Schwann cells", J. Biol. Chem., 280:11790-11797 (2005).

Ress, et al., "The PDZ protein erbin modulates beta-catenin-dependent transcription", Euro. Surgical Reaseach, 41:284-289 (2008).

Riethmacher, et al., "Severe neuropathies in mice with targeted mutations in the ErbB3 receptor", Nature, 389:725-730 (1997).

Roy, et al., "Loss of erbB signaling in oligodendrocytes alters myelin and dopaminergic function, a potential mechanism for neuropsychiatric disorders", Proc. Natl. Acad. Sci. USA, 104:8131-8136 (2007).

Schmucker, et al., "erbB3 is dispensable for oligodendrocyte development in vitro and in vivo". Glia., 44:67-75 (2003).

Shelly, et al., "Polar expression of ErbB-2/HER2 in epithelia. Bimodal regulation by Lin-7", Dev. Cell., 5:475-486 (2003).

Shy, "Peripheral neuropathies caused by mutations in the myelin protein zero", J. Neurol.; Sci., 242(1-2):55-66 (2006).

Tao, et al., "Erbin regulates NRG1 signaling and myelination", Proc. Natl. Sci. US, 106:9477-9482 (2009).

Taveggia, et al., "Type III neuregulin-1 promotes oligodendrocyte myelination", Glia., 56:284-293 (2008).

Taveggia, et al., "Neuregulin-1 type III determines the ensheathment fate of axons", Neuron., 47:681-94 (2005).

Tzashar, et al., "A hierarchical network of interreceptor interactions determines signal transduction by Neu differentiation factor/neuregulin and epidermal growth factor", Mol Cell Biol., 16:5276-5287 (1996).

Van Der Zee, et al., "Conditional deletion of the Itgb4 integrin gene in Schwann cells leads to delayed peripheral nerve regeneration", J. Neurosci., 28:11292-11303 (2008).

Weinstein and Wu, "Isolation and purification of primary Schwann cells", Curr. Protoc. Neurosci., Chapter 3, Unit 3 17 (2001).

Woldeyesus, et al., "Peripheral nervous system defects in erbB2 mutants following genetic rescue of heart development", Genes Dev., 13:2538-2548 (1999).

Wolpowitz, et al., "Cysteine-rich domain isoforms of the neuregulin-1 gene are required for maintenance of peripheral synapses", Neuron., 25:79-91 (2000).

Yang, et al., "Neuregulin-induced expression of the acetylcholine receptor requires endocytosis of ErbB receptors", Mol. Cell Neurosci., 28:335-346 (2005).

Yarden and Sliwkowski, "Untangling the ErbB signalling network", Nat. Rev. Mol. Cell Biol., 2:127-37 (2001).

* cited by examiner

SEQUENCE LISTING

```
<160> NUMBER OF SEQ ID NOS: 12

<210> SEQ ID NO 1
<211> LENGTH: 1371
<212> TYPE: PRT
<213> ORGANISM: Homo sapiens

<400> SEQUENCE: 1

Met Thr Thr Lys Arg Ser Leu Phe Val Arg Leu Val Pro Cys Arg Cys
1               5                   10                  15

Leu Arg Gly Glu Glu Thr Val Thr Thr Leu Asp Tyr Ser His Cys
            20                  25                  30

Ser Leu Glu Gln Val Pro Lys Glu Ile Phe Thr Phe Glu Lys Thr Leu
        35                  40                  45

Glu Glu Leu Tyr Leu Asp Ala Asn Gln Ile Glu Glu Leu Pro Lys Gln
    50                  55                  60

Leu Phe Asn Cys Gln Ser Leu His Lys Leu Ser Leu Pro Asp Asn Asp
65                  70                  75                  80

Leu Thr Thr Leu Pro Ala Ser Ile Ala Asn Leu Ile Asn Leu Arg Glu
                85                  90                  95

Leu Asp Val Ser Lys Asn Gly Ile Gln Glu Phe Pro Glu Asn Ile Lys
            100                 105                 110

Asn Cys Lys Val Leu Thr Ile Val Glu Ala Ser Val Asn Pro Ile Ser
        115                 120                 125

Lys Leu Pro Asp Gly Phe Ser Gln Leu Leu Asn Leu Thr Gln Leu Tyr
    130                 135                 140

Leu Asn Asp Ala Phe Leu Glu Phe Leu Pro Ala Asn Phe Gly Arg Leu
145                 150                 155                 160

Thr Lys Leu Gln Ile Leu Glu Leu Arg Glu Asn Gln Leu Lys Met Leu
                165                 170                 175
```

```
Pro Lys Thr Met Asn Arg Leu Thr Gln Leu Glu Arg Leu Asp Leu Gly
            180                 185                 190

Ser Asn Glu Phe Thr Glu Val Pro Glu Val Leu Glu Gln Leu Ser Gly
            195                 200                 205

Leu Lys Glu Phe Trp Met Asp Ala Asn Arg Leu Thr Phe Ile Pro Gly
            210                 215                 220

Phe Ile Gly Ser Leu Lys Gln Leu Thr Tyr Leu Asp Val Ser Lys Asn
225                 230                 235                 240

Asn Ile Glu Met Val Glu Gly Ile Ser Thr Cys Glu Asn Leu Gln
                245                 250                 255

Asp Leu Leu Leu Ser Ser Asn Ser Leu Gln Gln Leu Pro Glu Pro Ile
            260                 265                 270

Gly Ser Leu Lys Asn Ile Thr Thr Leu Lys Ile Asp Glu Asn Gln Leu
            275                 280                 285

Met Tyr Leu Pro Asp Ser Ile Gly Gly Leu Ile Ser Val Glu Glu Leu
        290                 295                 300

Asp Cys Ser Phe Asn Glu Val Glu Ala Leu Pro Ser Ser Ile Gly Gln
305                 310                 315                 320

Leu Thr Asn Leu Arg Thr Phe Ala Ala Asp His Asn Tyr Leu Gln Gln
                325                 330                 335

Leu Pro Pro Glu Ile Gly Ser Trp Lys Asn Ile Thr Val Leu Phe Leu
            340                 345                 350

His Ser Asn Lys Leu Glu Thr Leu Pro Glu Glu Met Gly Asp Met Gln
            355                 360                 365

Lys Leu Lys Val Ile Asn Leu Ser Asp Asn Arg Leu Lys Asn Leu Pro
        370                 375                 380

Phe Ser Phe Thr Lys Leu Gln Gln Leu Thr Ala Met Trp Leu Ser Asp
385                 390                 395                 400

Asn Gln Ser Lys Pro Leu Ile Pro Leu Gln Lys Glu Thr Asp Ser Glu
                405                 410                 415

Thr Gln Lys Met Val Leu Thr Asn Tyr Met Phe Pro Gln Gln Pro Arg
            420                 425                 430

Thr Glu Asp Val Met Phe Ile Ser Asp Asn Glu Ser Phe Asn Pro Ser
        435                 440                 445

Leu Trp Glu Glu Gln Arg Lys Gln Arg Ala Gln Val Ala Phe Glu Cys
450                 455                 460

Asp Glu Asp Lys Asp Glu Arg Glu Ala Pro Pro Arg Glu Gly Asn Leu
465                 470                 475                 480

Lys Arg Tyr Pro Thr Pro Tyr Pro Asp Glu Leu Lys Asn Met Val Lys
                485                 490                 495

Thr Val Gln Thr Ile Val His Arg Leu Lys Asp Glu Glu Thr Asn Glu
            500                 505                 510

Asp Ser Gly Arg Asp Leu Lys Pro His Glu Asp Gln Gln Asp Ile Asn
        515                 520                 525

Lys Asp Val Gly Val Lys Thr Ser Glu Ser Thr Thr Val Lys Ser
530                 535                 540

Lys Val Gly Glu Arg Glu Lys Tyr Met Ile Gly Asn Ser Val Gln Lys
545                 550                 555                 560

Ile Ser Glu Pro Glu Ala Glu Ile Ser Pro Gly Ser Leu Pro Val Thr
                565                 570                 575

Ala Asn Met Lys Ala Ser Glu Asn Leu Lys His Ile Val Asn His Asp
            580                 585                 590

Asp Val Phe Glu Glu Ser Glu Glu Leu Ser Ser Asp Glu Glu Met Lys
```

```
            595                 600                 605
Met Ala Glu Met Arg Pro Pro Leu Ile Glu Thr Ser Ile Asn Gln Pro
    610                 615                 620

Lys Val Ala Leu Ser Asn Asn Lys Lys Asp Asp Thr Lys Glu Thr
625                 630                 635                 640

Asp Ser Leu Ser Asp Glu Val Thr His Asn Ser Asn Gln Asn Asn Ser
                    645                 650                 655

Asn Cys Ser Ser Pro Ser Arg Met Ser Asp Ser Val Ser Leu Asn Thr
                660                 665                 670

Asp Ser Ser Gln Asp Thr Ser Leu Cys Ser Pro Val Lys Gln Thr His
            675                 680                 685

Ile Asp Ile Asn Ser Lys Ile Arg Gln Glu Asp Glu Asn Phe Asn Ser
        690                 695                 700

Leu Leu Gln Asn Gly Asp Ile Leu Asn Ser Ser Thr Glu Glu Lys Phe
705                 710                 715                 720

Lys Ala His Asp Lys Asp Phe Asn Leu Pro Glu Tyr Asp Leu Asn
                    725                 730                 735

Val Glu Glu Arg Leu Val Leu Ile Glu Lys Ser Val Asp Ser Thr Ala
                740                 745                 750

Thr Ala Asp Asp Thr His Lys Leu Asp His Ile Asn Met Asn Leu Asn
            755                 760                 765

Lys Leu Ile Thr Asn Asp Thr Phe Gln Pro Glu Ile Met Glu Arg Ser
        770                 775                 780

Lys Thr Gln Asp Ile Val Leu Gly Thr Ser Phe Leu Ser Ile Asn Ser
785                 790                 795                 800

Lys Glu Glu Thr Glu His Leu Glu Asn Gly Asn Lys Tyr Pro Asn Leu
                    805                 810                 815

Glu Ser Val Asn Lys Val Asn Gly His Ser Glu Glu Thr Ser Gln Ser
                820                 825                 830

Pro Asn Arg Thr Glu Pro His Asp Ser Asp Cys Ser Val Asp Leu Gly
            835                 840                 845

Ile Ser Lys Ser Thr Glu Asp Leu Ser Pro Gln Lys Ser Gly Pro Val
        850                 855                 860

Gly Ser Val Val Lys Ser His Ser Ile Thr Asn Met Glu Ile Gly Gly
865                 870                 875                 880

Leu Lys Ile Tyr Asp Ile Leu Ser Asp Asn Gly Pro Gln Gln Pro Ser
                    885                 890                 895

Thr Thr Val Lys Ile Thr Ser Ala Val Asp Gly Lys Asn Ile Val Arg
                900                 905                 910

Ser Lys Ser Ala Thr Leu Leu Tyr Asp Gln Pro Leu Gln Val Phe Thr
            915                 920                 925

Gly Ser Ser Ser Ser Asp Leu Ile Ser Gly Thr Lys Ala Ile Phe
        930                 935                 940

Lys Phe Asp Ser Asn His Asn Pro Glu Glu Pro Asn Ile Ile Arg Gly
945                 950                 955                 960

Pro Thr Ser Gly Pro Gln Ser Ala Pro Gln Ile Tyr Gly Pro Pro Gln
                    965                 970                 975

Tyr Asn Ile Gln Tyr Ser Ser Ser Ala Ala Val Lys Asp Thr Leu Trp
                980                 985                 990

His Ser Lys Gln Asn Pro Gln Ile Asp His Ala Ser Phe Pro Pro Gln
            995                 1000                1005

Leu Leu Pro Arg Ser Glu Ser Thr Glu Asn Gln Ser Tyr Ala Lys
        1010                1015                1020
```

-continued

```
His Ser Ala Asn Met Asn Phe Ser Asn His Asn Asn Val Arg Ala
    1025                1030                1035

Asn Thr Ala Tyr His Leu His Gln Arg Leu Gly Pro Ala Arg His
    1040                1045                1050

Gly Glu Met Trp Ala Ile Ser Pro Asn Asp Arg Leu Ile Pro Ala
    1055                1060                1065

Val Thr Arg Ser Thr Ile Gln Arg Gln Ser Ser Val Ser Ser Thr
    1070                1075                1080

Ala Ser Val Asn Leu Gly Asp Pro Gly Ser Thr Arg Arg Ala Gln
    1085                1090                1095

Ile Pro Glu Gly Asp Tyr Leu Ser Tyr Arg Glu Phe His Ser Ala
    1100                1105                1110

Gly Arg Thr Pro Pro Met Met Pro Gly Ser Gln Arg Pro Leu Ser
    1115                1120                1125

Ala Arg Thr Tyr Ser Ile Asp Gly Pro Asn Ala Ser Arg Pro Gln
    1130                1135                1140

Ser Ala Arg Pro Ser Ile Asn Glu Ile Pro Glu Arg Thr Met Ser
    1145                1150                1155

Val Ser Asp Phe Asn Tyr Ser Arg Thr Ser Pro Ser Lys Arg Pro
    1160                1165                1170

Asn Ala Arg Val Gly Ser Glu His Ser Leu Leu Asp Pro Pro Gly
    1175                1180                1185

Lys Ser Lys Val Pro Arg Asp Trp Arg Glu Gln Val Leu Arg His
    1190                1195                1200

Ile Gly Ala Lys Lys Leu Glu Lys Met Pro Leu Ser Asn Gly Gln
    1205                1210                1215

Met Gly Gln Pro Leu Arg Pro Pro Ala Asn Tyr Ser Gln Ile His
    1220                1225                1230

His Pro Pro Gln Ala Ser Val Ala Arg His Pro Ser Arg Glu Gln
    1235                1240                1245

Leu Ile Asp Tyr Leu Met Leu Lys Val Ala His Gln Pro Pro Tyr
    1250                1255                1260

Thr Gln Pro His Cys Ser Pro Arg Gln Gly His Glu Leu Ala Lys
    1265                1270                1275

Gln Glu Ile Arg Val Arg Val Glu Arg Asp Pro Glu Leu Gly Phe
    1280                1285                1290

Ser Ile Ser Gly Gly Val Gly Gly Arg Gly Asn Pro Phe Arg Pro
    1295                1300                1305

Asp Asp Asp Gly Ile Phe Val Thr Arg Val Gln Pro Glu Gly Pro
    1310                1315                1320

Ala Ser Lys Leu Leu Gln Pro Gly Asp Lys Ile Ile Gln Ala Asn
    1325                1330                1335

Gly Tyr Ser Phe Ile Asn Ile Glu His Gly Gln Ala Val Ser Leu
    1340                1345                1350

Leu Lys Thr Phe Gln Asn Thr Val Glu Leu Ile Ile Val Arg Glu
    1355                1360                1365

Val Ser Ser
    1370
```

<210> SEQ ID NO 2
<211> LENGTH: 24
<212> TYPE: DNA
<213> ORGANISM: Homo sapiens

<400> SEQUENCE: 2

```
ttgtcaagac cgacctgtcc ggtg                                          24

<210> SEQ ID NO 3
<211> LENGTH: 24
<212> TYPE: DNA
<213> ORGANISM: Homo sapiens

<400> SEQUENCE: 3
acgggtagcc aacgctatgt cctg                                          24

<210> SEQ ID NO 4
<211> LENGTH: 20
<212> TYPE: DNA
<213> ORGANISM: Homo sapiens

<400> SEQUENCE: 4
ctagttcaag gccagtctga                                               20

<210> SEQ ID NO 5
<211> LENGTH: 20
<212> TYPE: DNA
<213> ORGANISM: Homo sapiens

<400> SEQUENCE: 5
cagttagggt tgctggatta                                               20

<210> SEQ ID NO 6
<211> LENGTH: 24
<212> TYPE: DNA
<213> ORGANISM: Homo sapiens

<400> SEQUENCE: 6
cactctgtaa tcagttctta gcag                                          24

<210> SEQ ID NO 7
<211> LENGTH: 23
<212> TYPE: DNA
<213> ORGANISM: Homo sapiens

<400> SEQUENCE: 7
ggtaagacag aaactggcac cag                                           23

<210> SEQ ID NO 8
<211> LENGTH: 21
<212> TYPE: DNA
<213> ORGANISM: Homo sapiens

<400> SEQUENCE: 8
cactccaacc tccgcaaact c                                             21

<210> SEQ ID NO 9
<211> LENGTH: 24
<212> TYPE: DNA
<213> ORGANISM: Homo sapiens

<400> SEQUENCE: 9
gaaaatggca gagatgcgac ctcc                                          24

<210> SEQ ID NO 10
<211> LENGTH: 25
<212> TYPE: DNA
<213> ORGANISM: Homo sapiens

<400> SEQUENCE: 10
```

```
gacagtatcg gcctcaggaa gatcg                                          25

<210> SEQ ID NO 11
<211> LENGTH: 20
<212> TYPE: DNA
<213> ORGANISM: Homo sapiens

<400> SEQUENCE: 11
cgcgggtacc caagtgtgta                                                20

<210> SEQ ID NO 12
<211> LENGTH: 19
<212> TYPE: DNA
<213> ORGANISM: Homo sapiens

<400> SEQUENCE: 12
cgttgtccaa agggtctcg                                                 19
```

METHODS AND COMPOSITIONS FOR MODULATING ERBB2 ACTIVITY

CROSS REFERENCE TO RELATED APPLICATIONS

This application claims benefit of U.S. Provisional Application No. 61/216,218, filed May 14, 2009, which is hereby incorporated herein by reference in its entirety.

STATEMENT REGARDING FEDERALLY SPONSORED RESEARCH OR DEVELOPMENT

This invention was made with Government Support under Agreement NS44521 awarded to Dr. Lin Mei by the National Institutes of Health. The Government has certain rights in the invention.

FIELD OF THE INVENTION

The invention is generally related to the field of signal transduction, more particularly to methods and compositions for modulation ErbB2 activity.

BACKGROUND OF THE INVENTION

Human Epidermal growth factor Receptor 2 (HER2/ErbB2) is a protein giving higher aggressiveness in breast cancers. It is a member of the ErbB protein family, more commonly known as the epidermal growth factor receptor family. ErbB2 is a cell membrane surface-bound receptor tyrosine kinase and is normally involved in the signal transduction pathways leading to cell growth and differentiation. It is encoded within the genome by HER2/neu, a known proto-oncogene. The HER2/neu gene is a proto-oncogene located at the long arm of human chromosome 17(17q21-q22).

Approximately 15-20 percent of breast cancers have an amplification of the HER2/neu gene or overexpression of ErbB2. Overexpression of this receptor in breast cancer is associated with increased disease recurrence and worse prognosis. Overexpression also occurs in other cancer such as ovarian cancer, stomach cancer, and biologically aggressive forms of uterine ErbB2 also plays a role in neurological and psychiatric disorders. Impaired myelin formation and maintenance have been implicated in various neurological and psychiatric disorders including schizophrenia, multiple sclerosis, and Charcot-Marie-Tooth neuropathy disease (Mei L, et al. *Nat Rev Neurosci.* 2008 9:437-452; Shy Me. *J Neurol Sci.* 2006 242 (1-2):55-66). In the peripheral nervous system (PNS), neuregulin 1 (NRG1), which was originally identified as a 44-kD glycoprotein that interacts with the HER2/ErbB2 receptor tyrosine kinase, has emerged as a key axon-derived factor that regulates myelination. Disruption of NRG1 signaling by ablating either the EGF domain that is contained in all isoforms or type III isoform leads to an almost complete loss of Schwann cells (SCs) and of the sensory and motor neurons that they support (Meyer D, et al. *Nature.* 1995 378:386-390; Wolpowitz D, et al. *Neuron.* 2000 25:79-91). NRG1 does not actually interact with HER2/ErbB2 (Tzahar E, et al. *Mol Cell Biol.* 1996 16:5276-87). Instead, ErbB2 forms a heterodimer with ErbB3, which can bind NRG1 to be functional (Guy P M, et al. *Proc. Natl Acad Sci USA.* 1994 91:8132-86; Adlkofer K, et al. *Glia.* 2000 29:104-11). Mutation of NRG1, ErbB2, or ErbB3 genes causes severe deficits of peripheral neurons and SCs (Meyer D, et al. *Nature.* 1995 378:386 90; Wolpowitz D, et al. *Neuron.* 2000 25:79-91; Garratt A N, et al. *J Cell Biol.* 2000 148:1035-46; Lee K F, et al. *Nature.* 1995 378:394-98; Riethmacher D, et al. *Nature.* 1997 389:725-30; Woldeyesus M T, et al. *Genes Dev.* 1999 13:2538-48). Moreover, disruption of NRG1/ErbB signaling by a dominant negative approach leads to deficits in myelinating and nonmyelinating SCs (Chen S, et al. *Nat Neurosci.* 2003 6:1186-93; Chen S, et al. *J Neurosci.* 2006 26:3079-86).

The monoclonal antibody trastuzumab (Herceptin®) is a humanized monoclonal antibody that binds to the domain IV of the extracellular segment of the HER2/ErbB2 receptor. Cells treated with trastuzumab undergo arrest during the G1 phase of the cell cycle so there is reduced proliferation. It has been suggested that trastuzumab induces some of its effect by downregulation of HER2/ErbB2, leading to disruption of receptor dimerization and signaling through the downstream PI3K cascade. Another monoclonal antibody, Pertuzumab, which inhibits dimerization of HER2 and HER3 receptors, is in advanced clinical trials.

Unfortunately, treatment of breast cancers overexpressing ErbB2 with trastuzumab (Herceptin®) results in some patients developing cardiac dysfunction. The adverse effect is increased significantly in those patients who also receive the chemotherapeutical agent anthracycline. ErbB2-deficient cardiac myocytes are more susceptible to anthracycline-induced cytotoxicity (Negro, A, et al. *Recent Progress in Hormone Research* 2004 59:1-12). These results suggest that ErbB2 signaling in the heart is essential for the prevention of dilated cardiomyopathy. Thus, there is a need for new therapies for treating ErbB2-related disorders.

It is an object of the invention to provide alternative compositions and methods for modulating HER2/ErbB2 activity to treat HER2/ErbB2-mediated disorders or conditions.

It is another object of the invention to provide methods and compositions to treat HER2/ErbB2-mediated neurological disorders.

SUMMARY OF THE INVENTION

Modulating the interaction between ErbB2 and Erbin is an effective method for treating one or more symptoms of ErbB2-mediated disorders. It has been discovered that Erbin stabilizes ErbB2 in vivo and inhibiting the formation of heterodimers between Erbin and ErbB2 reduces or inhibits the biological activity of ErbB2 relative to control levels. Reducing the biological activity of ErbB2 is useful in the treatment of conditions characterized by the overexpression or misregulation of ErbB2. These conditions include, but are not limited to breast cancer and prostate cancer.

Alternatively, agonist of Erbin that promote or enhance the interaction of Erbin with ErbB2 can be useful in the treatment of certain neurological disorders. It has been discovered that Erbin plays a role in the myelination of neurons of the peripheral nervous system. Thus one embodiment provides a method of increasing peripheral neuron myelination by containing the peripheral neuron with an effective amount of an Erbin agonist to promote or enhanve myelination of the peripheral neuron.

Methods for identifying and selecting modulators of Erbin activity are also provided.

DETAILED DESCRIPTION OF THE INVENTION

1. Compositions for Modulating ErbB2 Activity

Figure 1A:
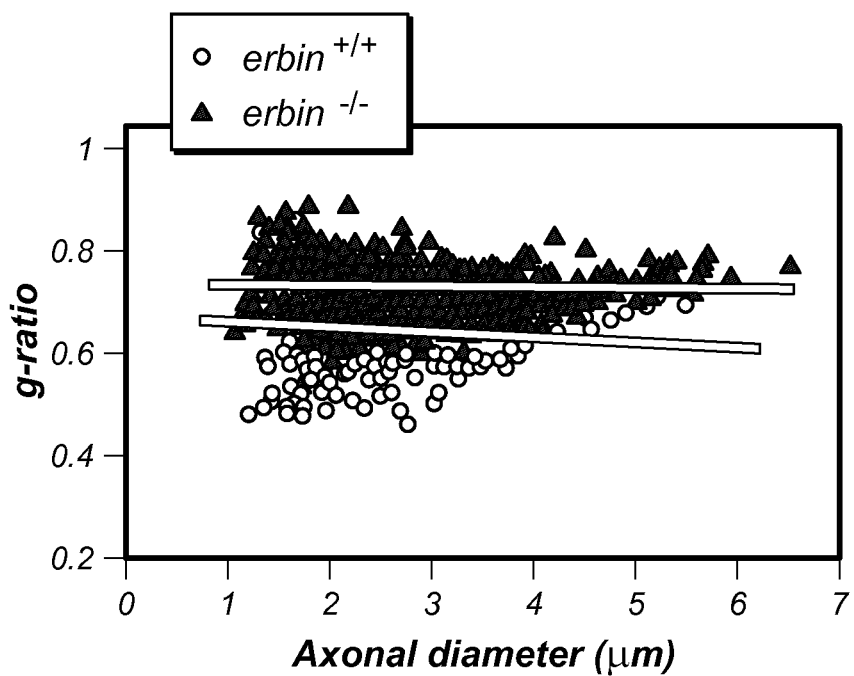
FIG. 1a is a graph showing g-ratio as a function of axonal diameter (μm) in erbin$^{+/+}$ (circle) and erbin$^{-/-}$ (triangle) mice.

Modulating the interaction between ErbB2 and Erbin is an effective method for treating one or more symptoms of ErbB2-mediated disorders. It has been discovered that Erbin stabilizes ErbB2 in vivo and inhibiting the formation of heterodimers between Erbin and ErbB2 reduces or inhibits the biological activity of ErbB2 relative to control levels. Reducing the biological activity of ErbB2 is useful in the treatment of conditions characterized by the overexpression or misregulation of ErbB2. These conditions include, but are not limited to breast cancer and prostate cancer.

A. Erbin Antagonists

In a preferred embodiment, the interaction between Erbin and ErbB2 can be inhibited or reduced by providing Erbin antagonists to one or more cells expressing ErbB2 and Erbin. The Erbin antagonist can be a polypeptide, aptamer or small molecule that binds Erbin or ErbB2 and inhibits for formation of heterodimers between the two. Preferably, the Erbin antagonist binds to the PDZ domain of Erbin or to the PDZ recognition domain of ErbB2. Alternatively, the Erbin antagonist can be an agent that reduces the expression of Erbin either pretranslationally or posttranslationally or reduces the bioavailability of Erbin.

Thus, the Erbin antagonist can be a polypeptide comprising the PDZ domain of Erbin but substantially lacking the N-terminal amino acids of Erbin, wherein the polypeptide binds ErbB2 under physiological conditions. The amino acid sequence of human Erbin is set forth in SEQ ID NO:1, shown below.

```
mttkrsifvr  lvpcrclrge  eetvttldys  hcsleqvpke
iftfektlee  lyldanqiee  lpkqlfncqs  lhklslpdnd
lttlpasian  linlreldvs  kngiqefpen  iknckvltiv
easvnpiskl  pdgfsqllnl  tqlylndafl  eflpanfgrl
tklqiielre  nqlkmlpktm  nrltqlerld  lgsneftevp
evleqlsglk  efwmdanrlt  fipgfigslk  qltyldvskn
niemveegis  tcenlqdlll  ssnslqqlpe  pigslknitt
lkidenqlmy  lpdsigglis  veeldcstne  vealpssigq
ltnlrtfaad  hnylqqlppe  igswknitvl  flhsnkletl
peemgdmqkl  kvinlsdnrl  knlpfsftkl  qqltamwlsd
nqskpliplq  ketdsetqkm  vitnymfpgq  prtedvmfis
dnesfnpslw  eeqrkgraqv  afecdedkde  reappregnl
kryptpypde  lknmvktvqt  ivhrlkdeet  nedsgrdlkp
nedqqdinkd  vgvktsestt  tvkskvgere  kymignsvqk
isepeaeisp  gslpvtanmk  asenlkhivn  hddvfeesee
lssdeemkma  emrppliets  inqpkvvals  nnkkddtket
dslsdevthn  snqnnsncss  psrmsdsysl  ntdssqdtsl
cspvkqthid  inskirqede  nfnsllqngd  ilnssteekf
kandkkdfnl  peydlnveer  lvlieksvds  tataddthkl
dhinmnlnkl  itndtfqpei  mersktqdiv  lgtsflsins
keetehleng  nkypnlesvn  kvnghseets  gspnrtephd
sdcsvdlgis  kstedlspqk  sgpvgsvvks  nsitnmeigg
lkiydilsdn  gpqqpsttvk  itsavdgkni  vrsksatlly
dqplqvftgs  ssssdlisgt  kaifkfdsnh  npeepniirg
ptsgpqsapq  iygppgyniq  ysssaavkdt  lwhskqnpqi
dhasfppqll  prsestenqs  yakhsanmnf  snhnnvrant
aynlhqrlgp  arhgemwais  pndrlipavt  rstiqrqssv
sstasvnlgd  pgstrraqip  egdylsyref  hsagrtppmm
pgsqrplsar  tysidgpnas  rpqsarpsin  eipertmsvs
dfnysrtsps  krpnarvgse  hslldppgks  kvprdwreqv
lrhigakkle  kmplsngqmg  gplrppanys  qihhppqasv
arhpsreqli  dylmlkvahq  ppytqphcsp  rqghelakqe
irvrverdpe  lgfsisggvg  grgnpfrpdd  dgifvtrvgp
egpaskllgp  gdkiigangy  sfiniehgga  vsllktfqnt
veliivrevs  s
```

Thus, the polypeptide can comprise amino acids 1307 to 1366 of SEQ ID NO:1, wherein the polypeptide comprises no more than 5 contiguous amino acids of amino acids 1-693 of SEQ ID NO:1. For example, the polypeptide can comprise amino acids 694-1371 of SEQ ID NO:1.

In some embodiments, the Erbin antagonist is a polypeptide comprising a PDZ binding domain, wherein the polypeptide binds Erbin under physiological conditions. For example, the Erbin antagonist can be a polypeptide comprising the PDZ binding domain of ErbB2, δ-catenin, or integrinβ4.

1. RNAi for Antagonizing Erbin

RNAi can be used to antagonize Erbin by inhibiting or downreagulating expression of Erbin from mRNA encoding Erbin. Thus, in some embodiments, the erbin antagonist is an RNAi that silences erbin gene expression.

RNAi includes small RNA molecules which are single stranded or double stranded RNA molecules generally less than 200 nucleotides in length. Such molecules are generally less than 100 nucleotides and usually vary from 10 to 100 nucleotides in length. In a preferred format, small RNA molecules have 11, 12, 13, 14, 15, 16, 17, 18, 19, 20, 21, 22, 23, 24, 25, 26, 27, 28, 29 or 30 nucleotides. Preferably, the nucleotides are contiguous, consecutive nucleotides of complementary to a target mRNA sequence, for example Erbin mRNA. Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded.

The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription product of siRNA to be expressed can be, for example, 15 to 49 bp, preferably 15 to 35 bp, and more preferably 21 to 30 bp long. The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. Nonpairing portions can be contained to the extent that they do not interfere with siRNA formation. The "bulge" used herein preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA or viral RNA, or an artificial RNA molecule.

In some embodiments, inhibitory double stranded RNA (dsRNA) is derived from an "exogenous template". Such a template may be all or part of a Erbin nucleotide sequence; it may be a DNA gene sequence or a cDNA produced from an mRNA isolated from a parasitic nematode, for example by reverse transcriptase. When the template is all or a part of a DNA gene sequence, it is preferred if it is from one or more or all exons of the gene. While the dsRNA is derived from an endogenous or exogenous template, there is no limitation on the manner in which it could be synthesized. For example, the siRNA can be chemically synthesized, produced by in vitro transcription; produced by digestion of long dsRNA by an RNase III family enzyme (e.g., Dicer, RNase III); expressed in cells from an siRNA expression plasmid or viral vector; or expressed in cells from a PCR-derived siRNA expression cassette SiRNA prepared in vitro is then introduced directly into cells by transfection, electroporation, or by another method. Alternatively, transfection of DNA-based vectors and cassettes that express siRNAs within the cells can be used. RNAi may be synthesized in vitro or in vivo, using manual and/or automated procedures. In vitro synthesis may be chemical or enzymatic, for example using cloned RNA polymerase (e.g., T3, T7, SP6) for transcription of the endogenous DNA (or cDNA) template, or a mixture of both.

In vivo, the dsRNA may be synthesised using recombinant techniques well known in the art (see e.g., Sambrook, et al., Molecular Cloning; A Laboratory Manual, Third Edition (2001)). For example, bacterial cells can be transformed with an expression vector which comprises the DNA template from which the dsRNA is to be derived. Alternatively, the cells, of a plant for example, in which inhibition of gene expression is required may be transformed with an expression vector or by other means. Bidirectional transcription of one or more copies of the template may be by endogenous RNA polymerase of the transformed cell or by a cloned RNA polymerase (e.g., T3, T7, SP6) coded for by the expression vector or a different expression vector. The use and production of an expression construct are known in the art (see WO98/32016; U.S. Pat. Nos. 5,593,874, 5,698,425, 5712, 135, 5,789,214, and 5,804,693). Inhibition of gene expression may be targeted by specific transcription in an organ, tissue, or cell type; an environmental condition (e.g. temperature, chemical); and/or engineering transcription at a developmental stage or age, especially when the dsRNA is synthesized in vivo in the plant cell for example. dsRNA may also be delivered to specific tissues or cell types using known gene delivery systems. Components of these systems include the seed-specific lectin promoter and the flower specific promoter from APETALA3. These vectors are listed solely by way of illustration of the many commercially available and well known vectors that are available to those of skill in the art.

If synthesized outside the cell, the RNA may be purified prior to introduction into the cell. Purification may be by extraction with a solvent (such as phenol/chloroform) or resin, precipitation (for example in ethanol), electrophoresis, chromatography, or a combination thereof. However, purification may result in loss of dsRNA and may therefore be minimal or not carried out at all. The RNA may be dried for storage or dissolved in an aqueous solution, which may contain buffers or salts to promote annealing, and/or stabilization of the RNA strands.

Suitable dsRNA can also contain one or more modified bases, or have a modified a backbone to increase stability or for other reasons. For example, the phosphodiester linkages of natural RNA may be modified to include at least one of a nitrogen or sulfur heteroatom. Moreover, dsRNA comprising unusual bases, such as inosine, or modified bases, such as tritylated bases, to name just two examples, can be used. It will be appreciated that a great variety of modifications have been made to RNA that serve many useful purposes known to those of skill in the art. The term dsRNA as it is employed herein embraces such chemically, enzymatically or metabolically modified forms of dsRNA, provided that it is derived from an endogenous template.

The double-stranded structure may be formed by a single self-complementary RNA strand or two separate complementary RNA strands. RNA duplex formation may be initiated either inside or outside the plant cell.

The sequence of at least one strand of the dsRNA contains a region complementary to at least a part of the target mRNA sufficient for the dsRNA to specifically hybridize to the target mRNA. In one embodiment, one strand of the siRNA is substantially identical to at least a portion of the target mRNA. "Identity", as known in the art, is the relationship between two or more polynucleotide (or polypeptide) sequences, as determined by comparing the sequences. In the art, identity also means the degree of sequence relatedness between polynucleotide sequences, as determined by the match between strings of such sequences. Identity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, N.J., 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide sequences, the term is well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. Applied Math., 48: 1073 (1988). Methods commonly employed to determine identity between sequences include, but are not limited to those disclosed in Carillo, H., and Lipman, D., SIAM J. Applied Math., 48:1073 (1988). Preferred methods to determine identity are designed to give the largest match between the sequences tested. Methods to determine identity are codified in computer programs. Computer program methods to determine identity between two sequences include, but are not limited to, GCG program package (Devereux, J., et al., Nucleic Acids Research 12(1): 387 (1984)), BLASTP, BLASTN, and FASTA (Atschul, S. F. et al., J. Molec. Biol. 215: 403 (1990)). Another software package well known in the art for carrying out this procedure is the CLUSTAL program. It compares the sequences of two polynucleotides and finds the optimal alignment by inserting spaces in either sequence as appropriate. The identity for an optimal alignment can also be calculated using a software package such as BLASTx. This program aligns the largest stretch of similar sequence and assigns a value to the fit. For any one pattern comparison several regions of similarity may be found, each having a different score. One skilled in the art will appreciate that two polynucleotides of different lengths may be compared over the entire length of the longer fragment. Alternatively small regions may be compared. Normally sequences of the same length are compared for a useful comparison to be made.

In one embodiment, the inhibitory nucleic acid has 100% sequence identity with at least a part of the target mRNA. However, inhibitory nucleic acids having 70%, 80% or greater than 90% or 95% sequence identity may be used. Thus sequence variations that might be expected due to genetic mutation, strain polymorphism, or evolutionary divergence can be tolerated.

The duplex region of the RNA may have a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

While the optimum length of the dsRNA may vary according to the target gene and experimental conditions, the duplex region of the RNA may be at least 19, 20, 21, 22, 23, 25, 50, 100, 200, 300, 400 or more nucleotides long.

2. Antibodies

Monoclonal and polyclonal antibodies that are reactive with epitopes of Erbin or ErbB2 and inhibit the interaction of Erbin with ErbB2 are also useful to antagonize Erbin activity. Thus, in some embodiments, the erbin antagonist is an antibody that specifically binds erbin and prevents erbin binding to ErbB2 under physiological conditions.

Monoclonal antibodies (mAbs) and methods for their production and use are described in Kohler and Milstein, Nature 256:495-497 (1975); U.S. Pat. No. 4,376,110; Hartlow, E. et al., Antibodies: A Laboratory Manual, Cold Spring Harbor Laboratory Press, Cold Spring Harbor, N.Y., 1988); Monoclonal Antibodies and Hybridomas: A New Dimension in Biological Analyses, Plenum Press, New York, N.Y. (1980); H. Zola et al., in Monoclonal Hybridoma Antibodies: Techniques and Applications, CRC Press, 1982)).

Immunoassay methods are described in Coligan, J. E. et al., eds., Current Protocols in Immunology, Wiley-Interscience, New York 1991 (or current edition); Butt, W. R. (ed.) Practical Immunoassay: The State of the Art, Dekker, N.Y., 1984; Bizollon, Ch. A., ed., Monoclonal Antibodies and New Trends in Immunoassays, Elsevier, N.Y., 1984; Butler, J. E., ELISA (Chapter 29), In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991; Weintraub, B., Principles of Radioimmunoassays, Seventh Training Course on Radioligand Assay Techniques, The Endocrine Society, March, 1986; Work, T. S. et al., Laboratory Techniques and Biochemistry in Molecular Biology, North Holland Publishing Company, NY, (1978) (Chapter by Chard, T., "An Introduction to Radioimmune Assay and Related Techniques").

Anti-idiotypic antibodies are described, for example, in Idiotypy in Biology and Medicine, Academic Press, New York, 1984; Immunological Reviews Volume 79, 1984; Immunological Reviews Volume 90, 1986; Curr. Top. Microbiol., Immunol. Volume 119, 1985; Bona, C. et al., CRC Crit. Rev. Immunol., pp. 33-81 (1981); Jerme, N K, Ann. Immunol. 125C:373-389 (1974); Jerne, N K, In: Idiotypes—Antigenson the Inside, Westen-Schnurr, I., ed., Editiones Roche, Basel, 1982, Urbain, J. et al., Ann. Immunol. 133D:179-(1982); Rajewsky, K. et al., Ann. Rev. Immunol. 1:569-607 (1983).

The antibodies may be xenogeneic, allogeneic, syngeneic, or modified forms thereof, such as humanized or chimeric antibodies. Antiidiotypic antibodies specific for the idiotype of a specific antibody, for example an anti-Erbin antibody, are also included. The term "antibody" is meant to include both intact molecules as well as fragments thereof that include the antigen-binding site and are capable of binding to an Erbin epitope. These include, Fab and F(ab')$_2$ fragments which lack the Fc fragment of an intact antibody, clear more rapidly from the circulation, and may have less non-specific tissue binding than an intact antibody (Wahl et al., *J. Nuc. Med.* 24:316-325 (1983)). Also included are Fv fragments (Hochman, J. et al. (1973) *Biochemistry* 12:1130-1135; Sharon, J. et al. (1976) *Biochemistry* 15:1591-1594). These various fragments are produced using conventional techniques such as protease cleavage or chemical cleavage (see, e.g., Rousseaux et al., *Meth. Enzymol.*, 121:663-69 (1986)).

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography.

The immunogen may include the complete Erbin polypeptides or fragments or derivatives thereof. Preferred immunogens include all or a part of the PDZ domain of Erbin. Immunogens including the PDZ domain are produced in a variety of ways known in the art, e.g., expression of cloned genes using conventional recombinant methods or isolation from cells of origin.

Monoclonal antibodies may be produced using conventional hybridoma technology, such as the procedures introduced by Kohler and Milstein, *Nature*, 256:495-97 (1975), and modifications thereof (see above references). An animal, preferably a mouse is primed by immunization with an immunogen as above to elicit the desired antibody response in the primed animal. B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of antibody of the desired specificity, e.g. by immunoassay techniques. Positive clones are subcloned, e.g., by limiting dilution, and the monoclonal antibodies are isolated.

Hybridomas produced according to these methods can be propagated in vitro or in vivo (in ascites fluid) using techniques known in the art (see generally Fink et al., *Prog. Clin. Pathol.*, 9:121-33 (1984)). Generally, the individual cell line is propagated in culture and the culture medium containing high concentrations of a single monoclonal antibody can be harvested by decantation, filtration, or centrifugation.

The antibody may be produced as a single chain antibody or scFv instead of the normal multimeric structure. Single chain antibodies include the hypervariable regions from an Ig of interest and recreate the antigen binding site of the native Ig while being a fraction of the size of the intact Ig (Skerra, A. et al. *Science,* 240: 1038-1041 (1988); Pluckthun, A. et al. *Methods Enzymol.* 178: 497-515 (1989); Winter, G. et al. *Nature,* 349: 293-299 (1991)). In a preferred embodiment, the antibody is produced using conventional molecular biology techniques.

3. Small Molecule Erbin inhibitors

The term "small molecule" refers to small organic compounds having a molecular weight of more than 100 and less than about 2,500 daltons, preferably between 100 and 2000, more preferably between about 100 and about 1250, more preferably between about 100 and about 1000, more preferably between about 100 and about 750, more preferably between about 200 and about 500 daltons. The small molecules often include cyclical carbon or heterocyclic structures and/or aromatic or polyaromatic structures substituted with one or more functional groups. The small molecule antagonists reduce or interfere with Erbin interacting with ErbB2 by binding to Erbin or binding to ErbB2.

Modulators of the function, expression, or bioavailability of the Erbin protein or gene and homologues thereof can be identified using well known techniques and reagents. Preferably the modulator inhibits physical interaction between Erbin and ErbB2.

In some embodiments, screening assays can include random screening of large libraries of test compounds. Alternatively, the assays may be used to focus on particular classes of compounds suspected of modulating the function or expression of Erbin or homologues thereof in cells, tissues, organs, or systems.

Assays can include determinations of Erbin expression, protein expression, protein activity, or binding activity. Other assays can include determinations of Erbin nucleic acid transcription or translation, for example mRNA levels, miRNA levels, mRNA stability, mRNA degradation, transcription rates, and translation rates.

In one embodiment, the identification of an Erbin modulator is based on the function of Erbin in the presence and absence of a test compound. The test compound or modulator can be any substance that alters or is believed to alter the function of Erbin, in particular the function of Erbin in the formation of heterdimers with ErbB2. Typically, a modulator will be selected that reduces, eliminates, or inhibits the formation of Erbin heterdimers.

One exemplary method includes contacting Erbin with at least a first test compound, and assaying for an interaction between Erbin and the first test compound with an assay.

Specific assay endpoints or interactions that may be measured in the disclosed embodiments include binding to ErbB2. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms such as *C. elegans* and transgenic animals.

Other screening methods include using labeled Erbin to identify a test compound. Erbin can be labeled using standard labeling procedures that are well known and used in the art. Such labels include, but are not limited to, radioactive, fluorescent, biological and enzymatic tags.

Another embodiment provides a method for identifying a modulator of Erbin expression by determining the effect a test compound has on the expression of Erbin in cells. For example isolated cells or whole organisms expressing Erbin can be contacted with a test compound. Erbin expression can be determined by detecting Erbin protein expression or Erbin mRNA transcription or translation. Suitable cells for this assay include, but are not limited to, immortalized cell lines, primary cell culture, or cells engineered to express Erbin. Compounds that modulate the expression of Erbin in particular that reduce or inhibit the expression or bioavailability of Erbin, can be selected. Alternatively, compounds that increase or enhance Erbin expression or activity can be selected.

One example of a cell free assay is a binding assay. While not directly addressing function, the ability of a modulator to bind to a target molecule, for example Etbin binding to ErbB2, in a specific fashion is strong evidence of a related biological effect. The binding of a molecule to a target may, in and of itself, be inhibitory, due to steric, allosteric or charge—charge interactions or may downregulate or inactivate Erbin. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Round polypeptide is detected by various methods.

4. Aptamers

In one embodiment, the antagonist of Erbin is an aptamer. Aptamers are oligonucleic acid or peptide molecules that bind to a specific target molecule. Aptamers are usually created by selecting them from a large random sequence pool. Peptide aptamers are proteins that are designed to interfere with other protein interactions inside cells, for example the interaction between Erbin and ErbB2. They include of a variable peptide loop attached at both ends to a protein scaffold. This double structural constraint greatly increases the binding affinity of the peptide aptamer to levels comparable to an antibody's (nanomolar range).

The variable loop length is typically composed of ten to twenty amino acids, and the scaffold may be any protein which has good solubility and compacity properties. Currently, the bacterial protein Thioredoxin-A is the most used scaffold protein, the variable loop being inserted within the reducing active site, which is a -Cys-Gly-Pro-Cys-loop in the wild protein, the two Cysteines lateral chains being able to form a disulfide bridge. Peptide aptamer selection can be made using different systems, but the most used is currently the yeast two-hybrid system.

B. Erbin Agonists

In certain embodiments, the increased or prolonged ErbB2 activity may be desired. In such circumstances agonists of Erbin are desirable. For example, Erbin has been discovered to be involved in myelination of neurons in the peripheral nervous system. Agonists of Erbin include compounds that increase the expression, bioavailability, or activity of Erbin. A preferred agonist of Erbin promotes or enhances the formation of Erbin heterdimers with ErbB2. In still another embodiment, the Erbin agonist enhances or promotes the stability or bioavailability of the Erbin/ErbB2 heterodimer.

II. Methods for Treating ErbB2-Mediated Disorders

The compositions disclosed herein can be used to treat one more symptoms associated with an ErbB2-mediated disorder or disease. Representative ErbB2-mediated disorders include, but are not limited to prostate cancer, breast cancer, and neurological disorders.

A. Cancer

The Erbin antagonists provided herein are generally useful in vivo and ex vivo for treating cancer by administering to subject an amount of a Erbin antagonist effective to inhibit or reduce the interaction of Erbin with ErbB2 in the subject. The types of cancer that may be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian, testicular and hematologic. Preffered cancers are prostate and breast cancer.

Thus, provided is a method of treating a cancer in a subject, wherein the cancer is characterized by ErbB2 overexpression, comprising administering to the subject a pharmaceutical composition comprising an erbin antagonist in a pharmaceutically acceptable exipient.

In some embodiments, the method further comprises administering to the subject an antibody that binds ErbB2. For example, the antibody can be trastuzumab or pertuzumab.

B. Neurological Disorders

In other embodiments, agonists of Erbin can be used to treat one or more symptoms of a neurological disease. For example, an agonist of Erbin can be administered to a subject to promote or increase myelination of peripheral neurons. Conditions that can be treated with Erbin agonists include, but are not limited to muscular dystrophy, cystic fibrosis, and myelin diseases. Agonists of Erbin can be Erbin protein, including recombinant Erbin, or fragments thereof, nucleic acid encoding Erbin protein, peptidomimetics of Erbin protein, or small molecules that promote one or more activities of Erbin. Other such Erbin agonists can be envisioned and are disclosed for use with the provided methods.

III. Formulations

A. Erbin Antagonist or Agonist Formulations

Pharmaceutical compositions including Erbin antagonists or agonist are provided. Pharmaceutical compositions containing peptides or polypeptides may be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration. The compositions may also be administered using bioerodible inserts and may be delivered directly to an appropriate lymphoid tissue (e.g., spleen, lymph node, or mucosal-associated lymphoid tissue) or directly to an organ or tumor. The compositions can be formulated in dosage forms appropriate for each route of administration. Compositions containing Erbin antagonists or agonist that are not peptides or polypeptides can additionally be formulated for enteral administration.

As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. Therapeutically effective amounts of Erbin antagonists or agonist inhibit or enhance the physical interaction between Erbin and ErbB2, respectively.

In a preferred embodiment, the Erbin antagonists or agonist is administered in a range of 0.1-20 mg/kg. A most preferred range is 5-20 mg of Erbin antagonists or agonist/kg. Generally, for intravenous injection or infusion, dosage may be lower than when administered by an alternative route.

1. Formulations for Parenteral Administration

In a preferred embodiment, the disclosed compositions, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Controlled Delivery Polymeric Matrices

Compositions containing one or more Erbin antagonist or agonist can be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel. The matrix can also be incorporated into or onto a medical device to modulate an immune response, to prevent infection in an immunocompromised patient (such as an elderly person in which a catheter has been inserted or a premature child) or to aid in healing, as in the case of a matrix used to facilitate healing of pressure sores, decubitis ulcers, etc.

Either non-biodegradable or biodegradable matrices can be used for delivery of Erbin antagonists or agonists, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

Controlled release oral formulations may be desirable. Erbin antagonists or agonists can be incorporated into an inert matrix which permits release by either diffusion or leaching mechanisms, e.g., films or gums. Slowly disintegrating matrices may also be incorporated into the formulation. Another form of a controlled release is one in which the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the active agent (or derivative) or by release of the active agent beyond the stomach environment, such as in the intestine. To ensure full gastric resistance an enteric coating (i.e, impermeable to at least pH 5.0) is essential. These coatings may be used as mixed films or as capsules.

The devices can be formulated for local release to treat the area of implantation or injection and typically deliver a dosage that is much less than the dosage for treatment of an entire body. The devices can also be formulated for systemic delivery. These can be implanted or injected subcutaneously.

3. Formulations for Enteral Administration

Erbin antagonists or agonist scan also be formulated for oral delivery. Oral solid dosage forms are known to those skilled in the art. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 21st Ed. (2005, Lippincott, Williams & Wilins, Baltimore, Md. 21201) pages 889-964. The compositions may be prepared in liquid form, or may be in dried powder (e.g., lyophilized) form. Liposomal or polymeric encapsulation may be used to formulate the compositions. See also Marshall, K. In: Modern Pharmaceutics Edited by G. S. Banker and C. T. Rhodes Chapter 10, 1979. In general, the formulation will include the active agent and inert ingredients which protect the PD-1 antagonist in the stomach environment, and release of the biologically active material in the intestine.

Liquid dosage forms for oral administration, including pharmaceutically acceptable emulsions, solutions, suspensions, and syrups, may contain other components including inert diluents; adjuvants such as wetting agents, emulsifying and suspending agents; and sweetening, flavoring, and perfuming agents.

B. Cancer Combination Therapies

The disclosed Erbin antagonists and antagonist compositions can be administered to a subject in need thereof alone or in combination with one or more additional therapeutic agents or combinations of the recited Erbin antagonists. The additional therapeutic agents are selected based on the condition, disorder or disease to be treated. For example, Erbin antagonists can be co-administered with one or more additional agents that function to treat one or more symptoms of a disorder or disease.

1. Chemotherapeutic Agents

The Erbin antagonist can also be combined with one or more additional therapeutic agents. Representative therapeutic agents include, but are not limited to chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotccan, lcucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

EXAMPLES

Example 1

Role of Erbin in Myelination

Materials and Methods
Reagents.
Antibodies (with catalog number) used are from NeoMarkers (neurofilament, MS-359), Generation of Erbin$^{-/-}$ and Erbin$^{\Delta C/\Delta C}$ Mice.

To generate erbin$^{-/-}$ mice, exons 1 and 2 of erbin gene were replaced in erbin-targeting vector by a neomycin-resistant marker flanked with LoxP sites. Erbin null ES cells 129 Ola were used to generated erbin$^{-/-}$ mice. To generate erbin$^{\Delta C/\Delta C}$ mice, Bga258 ES cells that contain the erbin gene disrupted by gene trapping using the pGT2Lxf vector, were obtained from BayGenomics. ES cell clones were transferred into mouse blastocysts. Chimeras that were generated from ES cells were crossed to C57/B16 mice, and the resulting heterozygous animals were crossed to produce homozygous mice. Mouse genotyping were performed by PCR with genomic DNA extracted from mouse tail tips. Primers used for erbin$^{-/-}$ mice genotyping are: Primers N1 (forward): 5'-TTGTC AAGAC CGACC TGTCC GGTG (SEQ ID NO:2); Primers N2 (reverse): 5'-ACGGG TAGCC AACGC TATGT CCTG (SEQ ID NO:3); Primers E1 (Forward): 5'-CTAGT TCAAG GCCAG TCTGA (SEQ ID NO:4); Primers E2 (reverse): 5'-CAGTT AGGGT TGCTG GATTA (SEQ ID NO:5). Primers used for erbin$^{\Delta C/\Delta C}$ mice genotyping are: Primer 6: 5'-CACTC TGTAA TCAGT TCTTA GCAG (SEQ ID NO:6); Primer 6': 5'-GGTAA GACAG AAACT GGCAC CAG (SEQ ID NO:7); and Primer 6": 5'-CACTC CAACC TCCGC AAACT C (SEQ ID NO 8).

EM Studies.

P30 mice were anesthetized and cardiac perfused with 4% formaldehyde and 2% glutaraldehyde in 0.1 M sodium cacodylate buffer (NaCac, pH 7.4). Sciatic nerves were removed and fixed overnight at 4° C. in the perfusion fixative. Twenty-four hours later, samples were washed by 0.1 MNaCac and osmicated with 2% osmium tetroxide 30-60 min at 4° C., washed by 0.1 M NaCac and by deionized $H_2O$ at 4° C., and dehydrated in graded (30-70%) ethanol. Samples were stained with 2% uranyl acetate in 70% ethanol at 4° C. for 30 min followed by dehydration with 70-100% ethanol. Samples were incubated with propylene oxide and embedded with embedding resins. Ultrathin sections were photographed with Phillips 400 Transmission electron microscope. EM images were analyzed by Image J (National Institutes of Health). To eliminate the bias on circularity, g-ratio of each axon was calculated by the perimeter of axons (inner) divided by the perimeter of corresponding fibers (outer). Axonal diameters were normalized by perimeters through equation: diameter=perimeter/$\pi$. This procedure allows for inclusion of irregularly-shaped axons and fibers and helps to eliminate biased measurement of diameters based on circularity. For quantitative analysis, cross sections of sciatic nerves were divided into 10 areas, and more than 2 images, randomly selected from each area, were examined.

Immunostaining and Immunoblotting.

Tissue sections were fixed in 4% PBS-buffered polyformaldhyde solution, and permeabilized with 0.3% Triton-X 100 and 3% goat serum in PBS. Samples were incubated with primary antibodies diluted in PBS containing 3% goat serum at 4° C. overnight. After washing with PBS for 3 times, samples were incubated with Alexa Fluor 488 goat anti-Rabbit or Alexa Fluor 594 goat anti-mouse secondary antibody for 1 h at room temperature. Samples were mounted with Vectashield mounting medium (Vector) and images were taken by Zeiss LSM510 confocal microscope. For immunoblotting, cells were lyzed and tissues homogenized in modified RIPA buffer (50 mM Tris_HCl, pH 7.4, 150 mM NaCl, 1% Nonidet P-40, 0.25% sodium deoxycholate, 1 mM PMSF, 1 mM EDTA, 5 mM sodium fluoride, 2 mM sodium orthovanadate, and protease inhibitors). Lysates were resolved on SDS/PAGE and transferred to nitrocellulose membranes. The membranes were blocked in PBS with 0.1% Tween-20 and 5% milk and incubated with indicated antibodies overnight at 4° C., and then with HRP-conjugated secondary antibody for 1 h at room temperature. Immunoreactive bands were visualized using enhanced chemiluminescence (Pierce). Autoradiographic films were scanned with an Epson 1680 scanner, and the captured image was analyzed with Image Quant 5.2 (Molecular Dynamics).

Conduction Velocity and Von Frey Fiber/Sensory Test.

Tail conduction velocity was recorded at stringently controlled tail surface temperatures (23-24° C.). The time between a stimulus and action potential includes nerve conduction and that of non-nerve tissues such as fat, muscle and skin tissues. To eliminate the variation by non-nerve tissues, tails were stimulated by 2 ring electrodes at different proximal locations. Conduction was recorded by an electrode placed at the distal region, with tail tips grounded by a clip electrode. Electrical pulses propagated on tail nerves were recorded by Nicolet VikingQuest. Conduction velocity was calculated by the program preset in VIASYS Healthcare NeuroCare. For sensory tests, hindpaws were stimulated by Von Frey Hair (Stoelting). The withdrawal of the paw or a brisk movement of mouse body was taken as positive response.

Results

To study the function of Erbin, Erbin expression was examined in various tissues. DRG, sciatic nerves, white matter (medulla and corpus callosum) and gray matter (top layers of cortex) were isolated from an adult mouse and homogenized. Homogenates were subjected to SDS/PAGE and probed for Erbin. GADPH was probed to indicate equal loading. Sciatic nerves were isolated from an adult mouse, cross-sectioned, and stained with polyclonal antibodies against Erbin and monoclonal antibodies against neurofilament.

Erbin expression in sciatic nerves was higher than that in dorsal root ganglions (DRG); and in the brain, it was expressed at higher levels in the white matter than in the gray matter. These results indicate that Erbin is enriched in regions where myelinated axons are abundant. This notion was supported by immunohistochemical staining of transverse cross-sections of sciatic nerves. Erbin immunoreactivity was detected almost exclusively in myelin rings, not in axons, of sciatic nerves.

Figure 5:
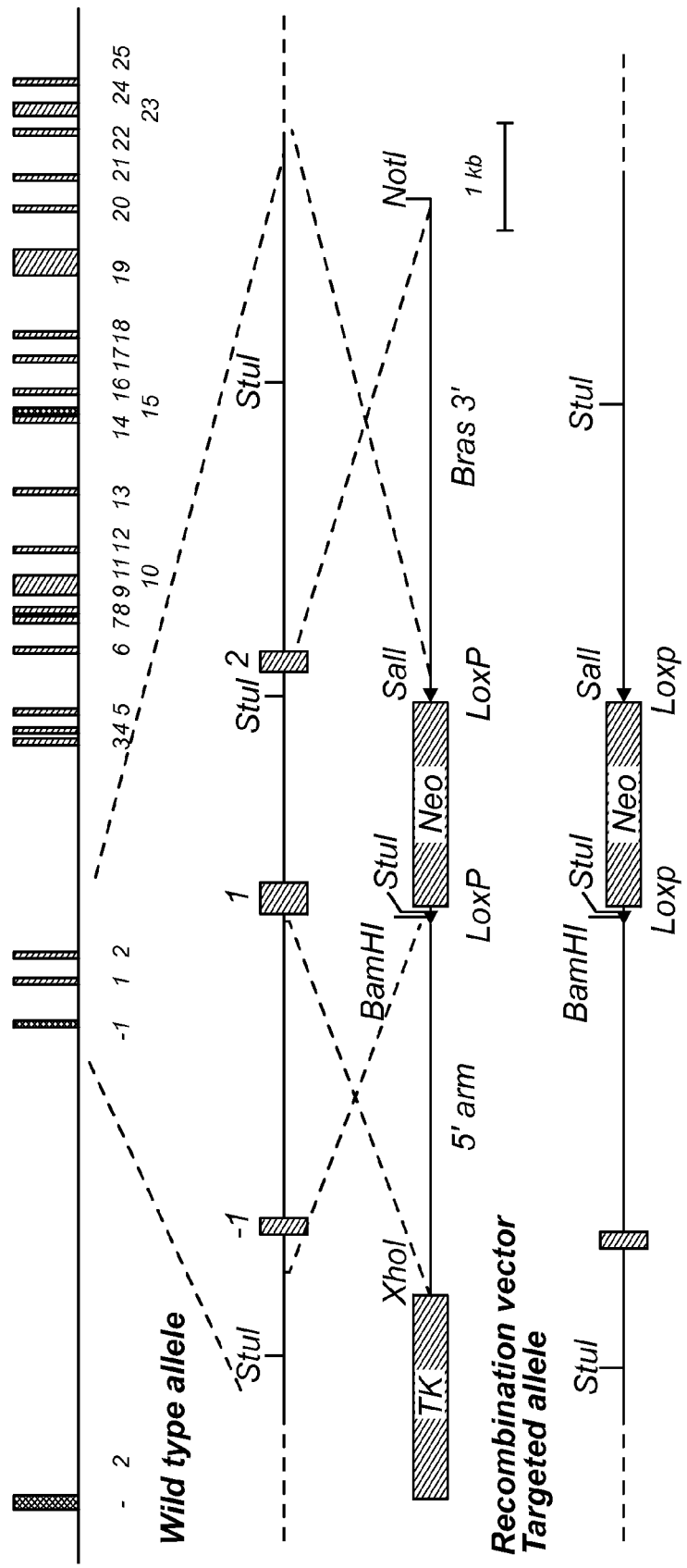
FIG. 5 is a schematic diagram illustrating the strategy to generate Erbin null allele for erbin$^{-/-}$ mice.

To study the role of Erbin in myelination, Erbin null mutant mice [erbin$^{-/-}$ (FIG. 5)] were generated. Electron micrographs of sciatic nerve cross sections of erbin$^{-/-}$ mice were examined at 1 month old. Unless otherwise indicated, control mice were age-controlled wild-type littermates. Remarkably, myelin of axons was significantly thinner in erbin$^{-/-}$ mice in comparison with that of erbin$^{+/+}$ littermates, indicating impaired myclination in Erbin mutant mice.

To analyze the deficits quantitatively, g-ratios (axon diameters/fiber diameters of myelinated axons) were measured. Three pairs of littermates, and ≈250 axons for each mouse, were analyzed. Averaged g-ratio in erbin$^{+/+}$ mice was 0.656±0.0135 (n=278), in agreement with previous reports (Michailov G V, et al. *Science*. 2004 304:700-03; Taveggia C, et al. *Neuron*. 2005 47:681-94; Chen S, et al. *J Neurosci*. 2006 26:3079-86). Significantly, it was increased to 0.740±0.0153 in erbin$^{-/-}$ mice (n=206, P<0.001), indicating reduced myelin thickness in erbin$^{-/-}$ mice. The reduction in myelin thickness was observed in axons of different sizes ranging from 1 to 7 µm as revealed by the scatter plot of g-ratios of individual fibers versus of axon diameters (FIG. 1a). The ultrastructure and periodicity of compact myelin showed no apparent difference from that of control littermates, indicating that impaired myelination in erbin$^{-/-}$ sciatic nerves results from the reduced number of myelin lamellae, but not radial sorting (the 1:1 association of SCs to axons), myelin initiation or compaction.

Figure 6A:
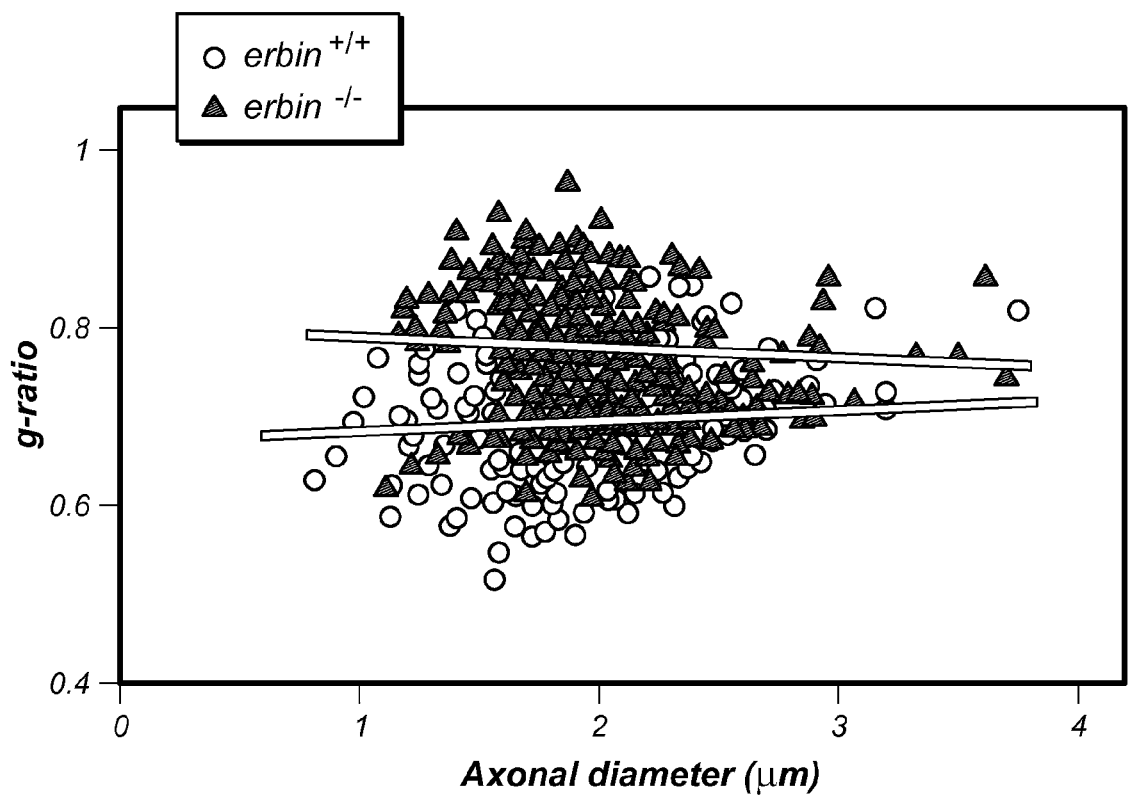
FIG. 6a is a graph showing g-ratio as a function of axonal diameter (m) in erbin$^{+/+}$ (circles) and erbin$^{\Delta C/\Delta C}$ (squares) mice at postnatal stage P8.
Figure 6B:
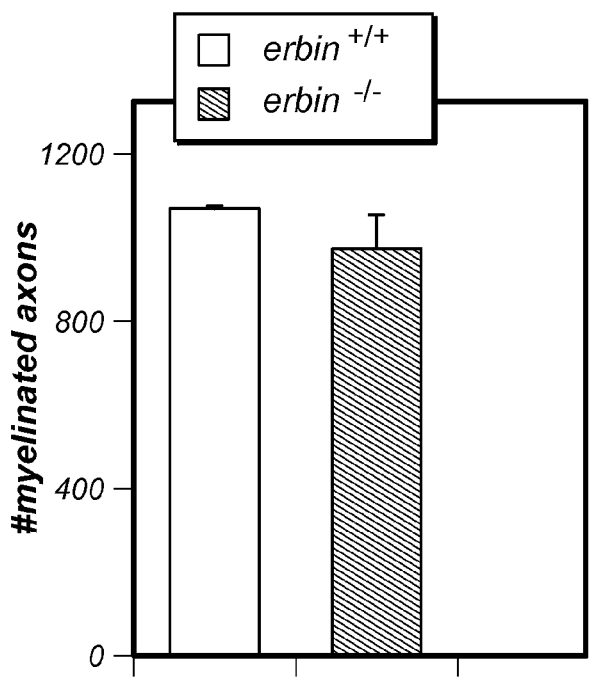
FIG. 6b is a bar graph showing the number of myelinated axons in random areas of EM pictures of sciatic nerves from erbin$^{+/+}$ (left bars) and erbin$^{-/-}$ (right bars) sciatic nerves at postnatal stage P8.

In agreement, erbin$^{-/-}$ sciatic nerves at postnatal day 8 (P8) showed deficits in myelination and increased g-ratios (FIG. 6a). Averaged g-ratio changed from 0.712±0.0139 (n=347) in sciatic nerves of erbin$^{+/+}$ littermates to 0.766±0.0136 (n=379, P<0.001) in those of erbin$^{-/-}$ mice at P8. However, many SCs associated with single axons, indicating proper radial sorting. Importantly, at this stage, the number of myelinated axons was similar between erbin$^{-/-}$ and control littermates (FIG. 6b), indicating that myelin initiation is normal in erbin$^{-/-}$ mutant mice.

Figure 1B:
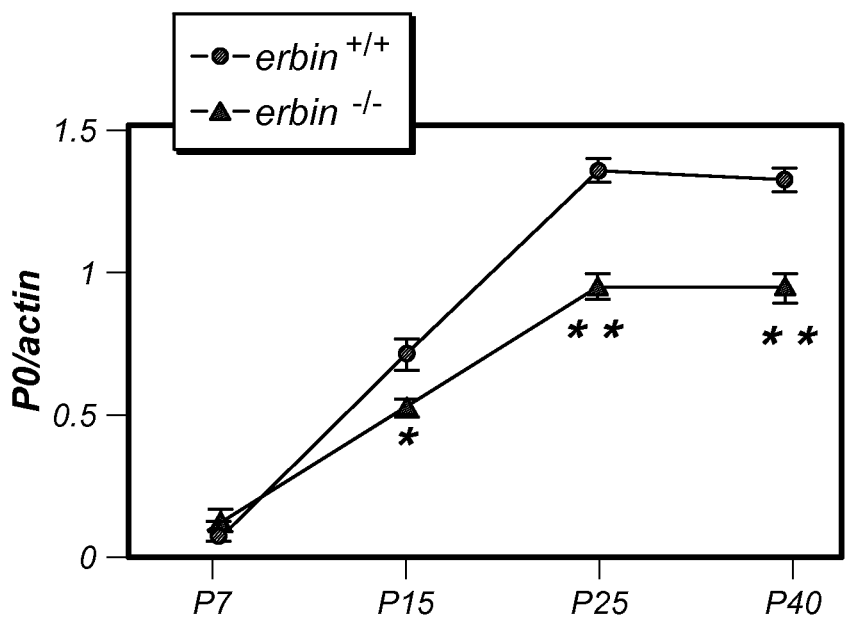
FIG. 1b is a graph showing relative Myelin protein zero (P0) expression normalized to β-actin as a function of postnatal stage (P7, P15, P25, P40) in erbin$^{+/+}$ (circle) and erbin$^{-/-}$ (triangle) mice. n=3, * P<0.05;  P<0.01.

Homogenates of sciatic nerves from erbin$^{-/-}$ or age-controlled littermates were subjected to SDS/PAGE and probed for the P0 protein, and β-actin to indicate equal loading. Consistent with myelin deficits in morphologic studies, the expression of P0, a major structural protein for peripheral compact myelin (Shy Me. *J Neurol Sci*. 2006 242(1-2):55-66), was significantly lower in erbin$^{-/-}$ sciatic nerves than that in wild-type littermates during development (FIG. 1b).

Figure 1C:
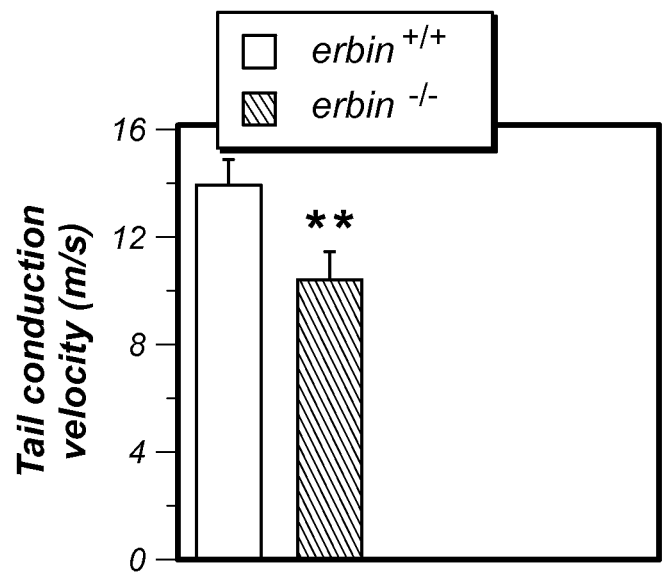
FIG. 1c is a bar graph showing tail conduction velocity (m/s) in erbin$^{+/+}$ (left bar) and erbin$^{-/-}$ (right bar) mice. n=4,  P<0.01.
Figure 1D:
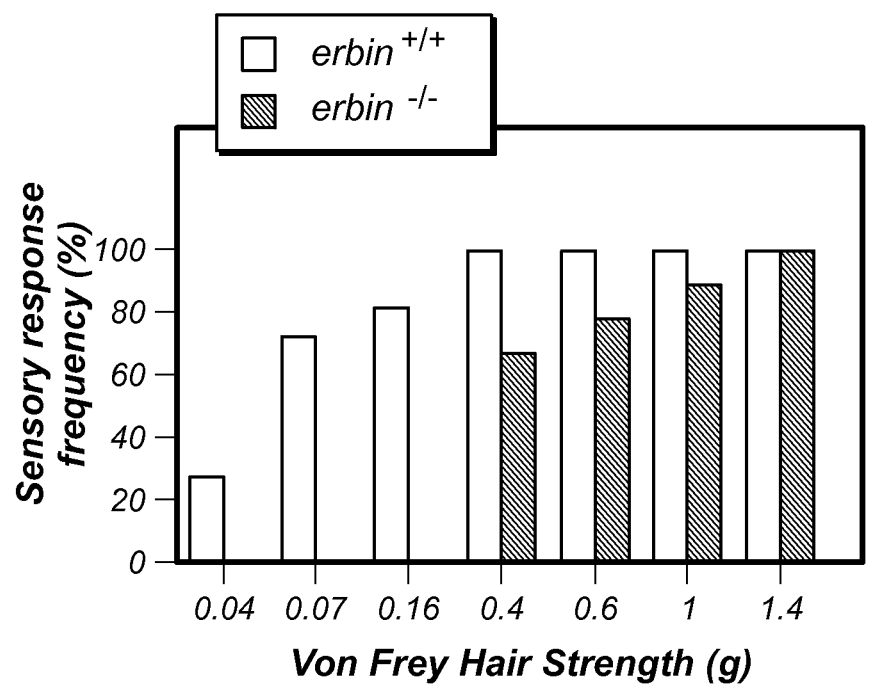
FIG. 1d is a bar graph showing percentages of mice responding to Von Frey Hair stimulation as a function of Von Frey Hair Strength (g) for erbin$^{+/+}$ (left bars) and erbin$^{-/-}$ (right bars) mice. n=8 mice in each group.

Thus, myelination is impaired when Erbin is mutated in mice. To investigate whether Erbin mutation alters nerve function, action potentials propagating along tail nerves were recorded under a condition that eliminated influence by non-nerve tissues and temperature variation. As shown in FIG. 1c, nerve conduction velocity was significantly reduced in erbin$^{-/-}$ mice, indicating functional impairment. In addition, sensory threshold, smallest strength of Von Frey Hair to generate 80% hindpaw response, was increased in erbin$^{-/-}$ mice (FIG. 1d). Together, these results demonstrate that Erbin is essential for myelination and proper function of peripheral nerves.

Figure 1E:
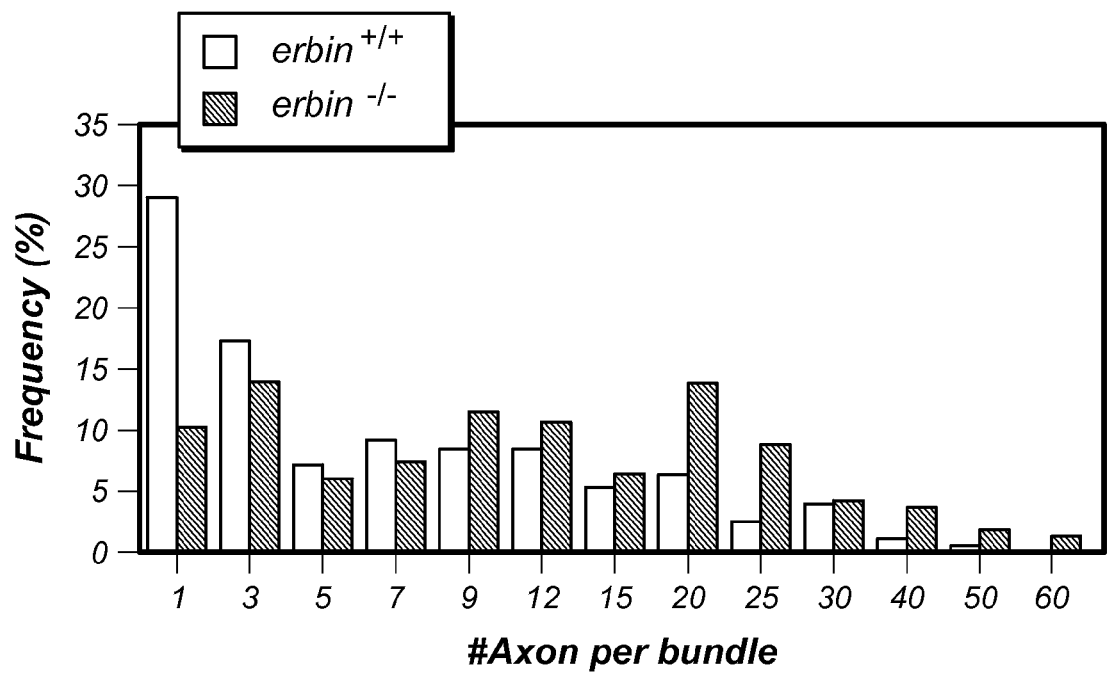
FIG. 1e is a bar graph showing the frequency (percentage) of mice as a function of the number of unmyelinated axons in Remak bundles in erbin$^{+/+}$ (left bars) and erbin$^{-/-}$ bars) sciatic nerves. Remak bundles analyzed were 255 for erbin$^{+/+}$ and 216 for erbin$^{-/-}$.
Figure 1F:
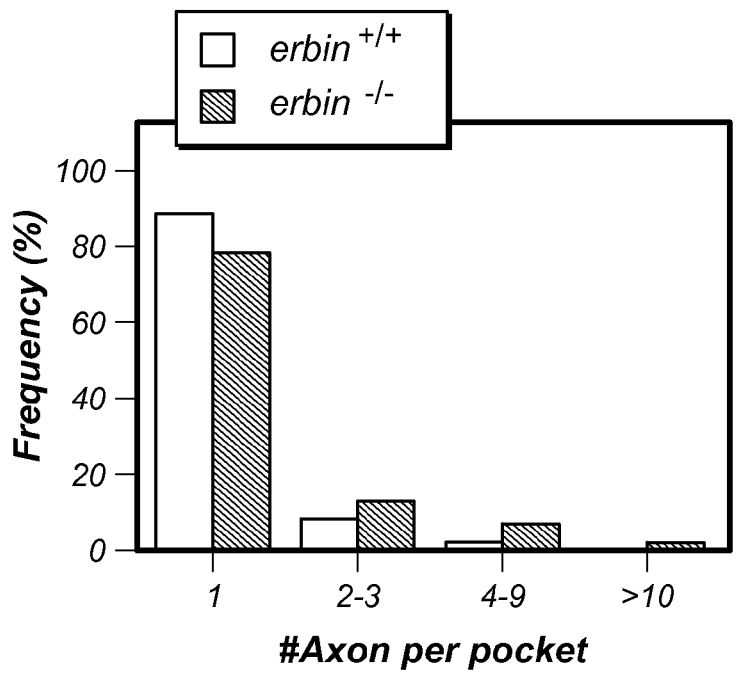
FIG. 1f is a graph showing the frequency (percentage) of mice as a function of the number of unmyelinated axons in SC pockets in erbin$^{+/+}$ (left bars) and erbin$^{-/-}$ (right bars) sciatic nerves. Pockets analyzed were 1602 for erbin$^{+/+}$ and 1245 for erbin$^{-/-}$.
Figure 1G:
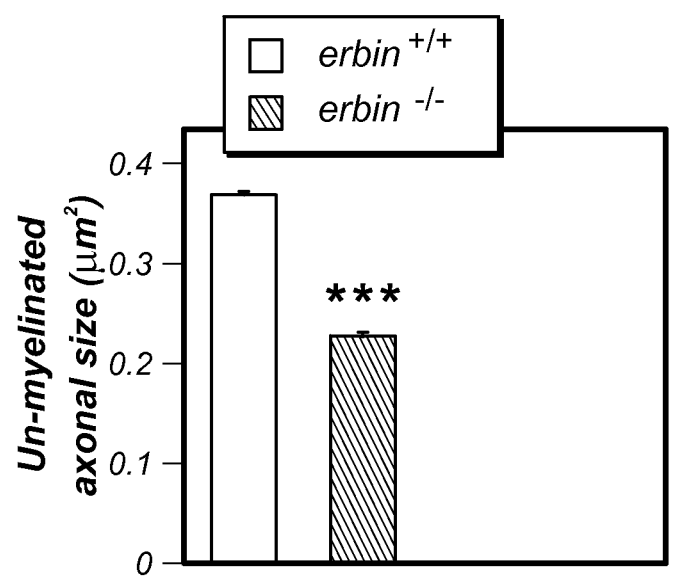
FIG. 1g is a graph showing the unmyelinated axonal size ($\mu m^2$) in erbin$^{+/+}$ (left bar) and erbin$^{-/-}$ (right bar) sciatic nerves. *** P<0.001.

In addition to large (≧1 µm) myelinated axons, there are small axons, such as C fibers that conduct nociceptive signal and are ensheathed by nonmyelinating SCs (Taveggia C, et al. *Neuron*. 2005 47:681-94; Chen S, et al. *Nat Neurosci*. 2003 6:1186-93). It was investigated whether Erbin is necessary for ensheathment of unmyelinated axons. In wild-type mice, unmyelinated axons are clustered in Remak bundles that were sporadically located among myelinated fibers. Most bundles contained <20 axons; and 90% of axons were ensheathed into individual pockets (FIGS. 1e and 1f). In contrast, the number of unmyelinated axons was significantly increased in Remak bundles in erbin$^{-/-}$ sciatic nerves. Quantitative analyses indicated a right-ward shift of the distribution of the number of axons per bundle (FIG. 1e). Furthermore, the percentage of pockets containing more axons was significantly increased in erbin$^{-/-}$ sciatic nerves (FIG. 1f) where axons were compacted to each other and not completely segregated. In addition, the averaged size of unmyelinated axons was smaller in sciatic nerves of erbin$^{-/-}$ mice (FIG. 1g), presumably because of lack of support from nonmyelinating SCs. These results indicate deficient ensheathment by nonmyelinating SCs in erbin$^{-/-}$ mice, indicating a critical role of Erbin in this event.

Example 2

Erbin Regulates ErbB2 Stability and Internalization

Materials and Methods

Reagents.

Antibodies (with catalog number) used are from BD Transduction Laboratories (δ-catenin, C98320), and Santa Cruz Biotechnology (ErbB2, sc-284; ErbB3, sc-285; NRG1, sc-348; Integrinβ4, se-9090).

RT-PCR.

Total RNA was extracted from pooled mouse sciatic nerves with TRIzol (Invitrogen) according to the manufacture's instruction. cDNA and PCR products were generated by Super-Script III One-Step RT-PCR System with Platinum TaqDNA Polymerase (Invitrogen). erbin$_{1-693}$βgal transcripts were detected using forward primer P20 on exon 20 (5'-GAAAA TGGCA GAGAT GCGAC CTCC, SEQ ID NO:9) and reverse primer β-geo on pGT2Lxf trapping vector (5'-GACAG TATCG GCCTC AGGAA GATCG, SEQ ID NO:10), which generated a product of 604 bp. For erbB2 transcripts, primers were 5'-CGCGG GTACC CAAGT GTGTA (forward, SEQ ID NO:11)) and 5'-CGTTG TCCAA AGGGT CTCG (reverse, SEQ ID NO:12), which generated a product of 326 bp.

Results

To investigate mechanisms by which Erbin deficiency impairs myelination and ensheathment, expression of Erbin-interacting proteins were examined. Erbin, via the PDZ domain, interacts with integrinβ4, a receptor for laminins, which are the components of extracellular matrix (Favre B, et al. *J Biol Chem*. 2001 276:32427-36), δ-catenin, a member of the p120 catenin family, which is critical for adherence junction formation (Laura R P, et al. *J Biol Chem*. 2002 277: 12906-114), and ErbB2 (Yarden Y, et al. Nat Rev Mol Cell Biol. 2001 2:127-37), all of which are implicated in myelin formation or regeneration (Garratt A N, et al. *J Cell Biol*. 2000 148:1035-46; Perrin-Tricaud C, et al. *Mol Cell Neurosci*. 2007 35:120-29; Van der Zee C E, et al. *J Neurosci*. 2008 28:11292-303). It also interacts with EBP50, an adherence junction protein implicated in SC motility (Rangwala R, et al. *J Biol Chem*. 2005 280:11790-97; Gatto C L, et al. *J Cell Physiol*. 2007 210:122-32).

Figure 2A:
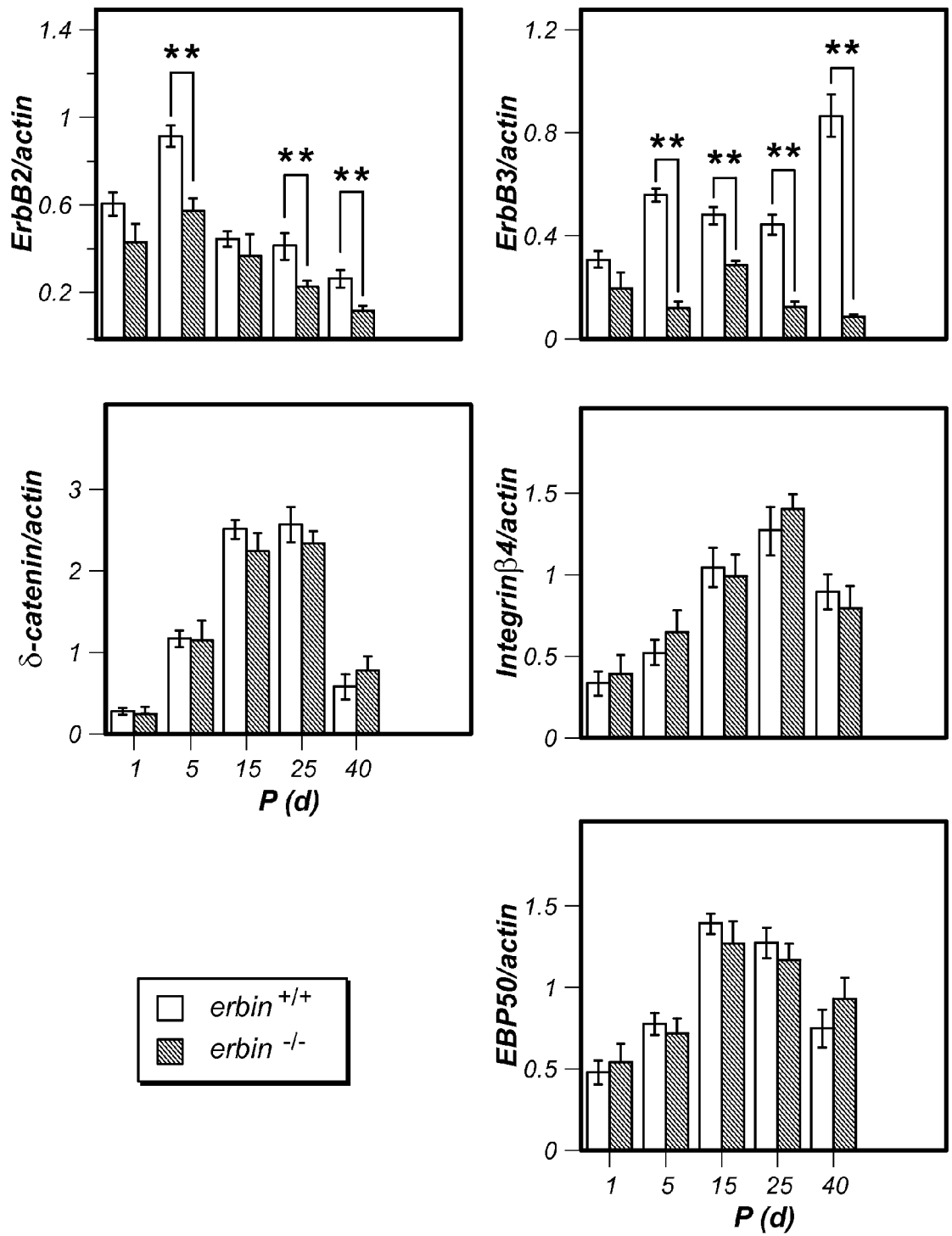
FIG. 2a contains bar graphs showing relative expression of ErbB2 (top left graph), δ-catenin (middle left graph), ErbB3 (top right graph), Integrinβ4 (middle right graph), and EBP50 (bottom graph) normalized to β-actin as a function of postnatal stage (P1, P5, P15, P25, P40) in erbin$^{+/+}$ (left bars) and erbin$^{-/-}$ (right bars) sciatic nerves. n=3, ** P<0.01.

Sciatic nerves at different ages were homogenized and analyzed for expression of Erbin, ErbB2, ErbB3, Integrinβ4, EBP50, and δ-catenin by immunoblotting. β-actin was also probed to indicate equal loading. Temporal expression of Erbin did not correlate with that of integrinβ4, δ-catenin, and EBP50 in developing wild-type sciatic nerves. Moreover, levels of the 3 proteins showed no difference between wild-type and erbin$^{-/-}$ sciatic nerves (FIG. 2a). In contrast, ErbB2 expression pattern was similar to that of Erbin, both of which peaked at P5 and gradually reduced after that. Intriguingly, levels of ErbB2 were reduced in erbin$^{-/-}$ sciatic nerves (FIG. 2a).

Figure 2B:
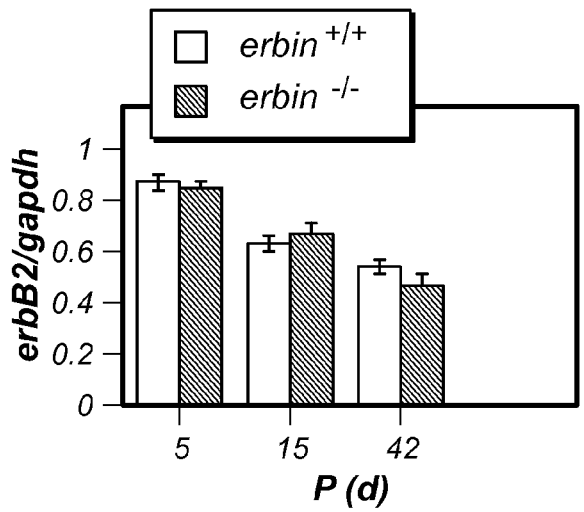
FIG. 2b is a bar graph showing relative expression of erbB2 mRNA normalized to gapdh as a function of postnatal stage (P5, P15, P42) in erbin$^{+/+}$ (left bars) and erbin$^{-/-}$ (right bars) sciatic nerves. n=3.
Figure 2C:
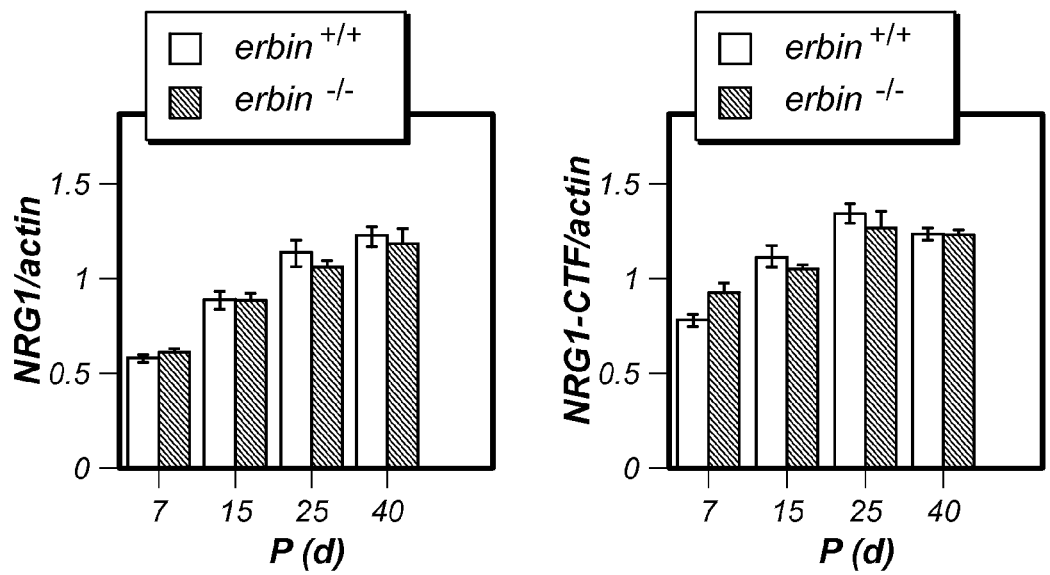
FIG. 2c contains bar graphs showing relative expression of neuregulin 1 (NRG1, left graph) and its C-terminal fragment (NRG1-CTF, right graph) normalized to β-actin as a function of postnatal stage (P7, P15, P25, P40) in erbin$^{+/+}$ (left bars) and erbin$^{-/-}$ (right bars) sciatic nerves. n=3.

Considering that ErbB2 is an important component of NRG1 receptor in SCs and NRG1 is important for myelination (Mei L, et al. *Nat Rev Neurosci*. 2008 9:437-52; Adlkofer K, et al. *Glia*. 2000 29:104-11), these results suggest that ErbB2 may be a target of Erbin deficiency. Total RNA was thus purified and subjected to RT-PCR using specific primers of erbB2 and gapdh. The reduction of ErbB2 did not appear to result from impaired transcription of the ErbB2 gene because ErbB2 mRNA levels were similar between wild-type and erbin$^{-/-}$ sciatic nerves (FIG. 2b), indicating that the reduction of ErbB2 proteins in erbin$^{-/-}$ sciatic nerves was due to a posttranscriptional mechanism. ErbB3, the other ErbB kinase in SCs that forms a heterodimer with ErbB2, was also reduced in erbin$^{-/-}$ sciatic nerves (FIG. 2a). These results indicate that NRG1 signaling that is critical for SC development and myelination (Michailov G V, et al. *Science.* 2004 304:700-03; Adlkofer K, et al. *Glia.* 2000 29:104-11) was compromised in the mutant mice. The idea was supported by observations that similar myelin deficits exhibit in type III NRG1 hypomorphic mice and mice that express a dominant negative (DN) ErbB4 mutant (Michailov G V, et al. *Science.* 2004 304:700-03; Taveggia C, et al. *Neuron.* 2005 47:681-94; Chen S, et al. *Nat Neurosci.* 2003 6:1186-93; Chen S, et al. *J Neurosci.* 2006 26:3079-86). Note that Erbin deletion did not alter NRG1 expression (FIG. 2c). Levels of full length NRG1 and its C-terminal fragment (NRG1-CTF) in erbin$^{-/-}$ sciatic nerves were similar to those in wild-type littermates. These results indicate that Erbin mutation specifically reduces NRG1 receptors in developing SCs.

Example 3

Figure 3A:
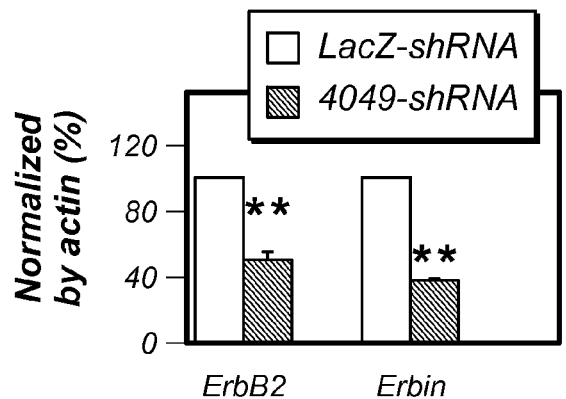
FIG. 3a is a bar graph showing relative expression of ErbB2 (left set of bars) and Erbin (right set of bars) normalized to β-actin in HEK293 cells transfected with 4049-shRNA (right bars) and control LacZ-shRNA (left bars). n=3;  P<0.01 compared with lacZ-shRNA-transfected cells.

Materials and Methods
Reagents.
pFlag-ErbB2, pcDNA3-ErbB3, pEF6-Erbin, pRK5, pRK5-Erbin/PDZ (Erbin965), pU6-lacZshRNA and pU6-4049-shRNA are described (Dai P, et al. *J Biol Chem* 281: 927-33; Yang X L, et al. *Mol Cell Neurosci* 28:335-46). Antibodies (with catalog number) used are from Abcam (EBP50, ab3452).
Results
To investigate mechanisms by which Erbin deficiency reduces ErbB2, Erbin levels were manipulated to examine if ErbB2 stability is altered. Cells were transfected with 4049-shRNA (Dai P, et al. *J Biol Chem.* 2006 281:927-33), short hairpin RNA that inhibits Erbin expression (FIG. 3a). Specifically, HEK293 cells were transfected with 4049-shRNA and control LacZ-shRNA. Seventy-two hours after transfection, cells were lyzed and lysates were probed for ErbB2, Erbin, and β-actin. Such transfected cells expressed less ErbB2 (FIG. 3a), in agreement with in vivo studies.

Figure 3B:
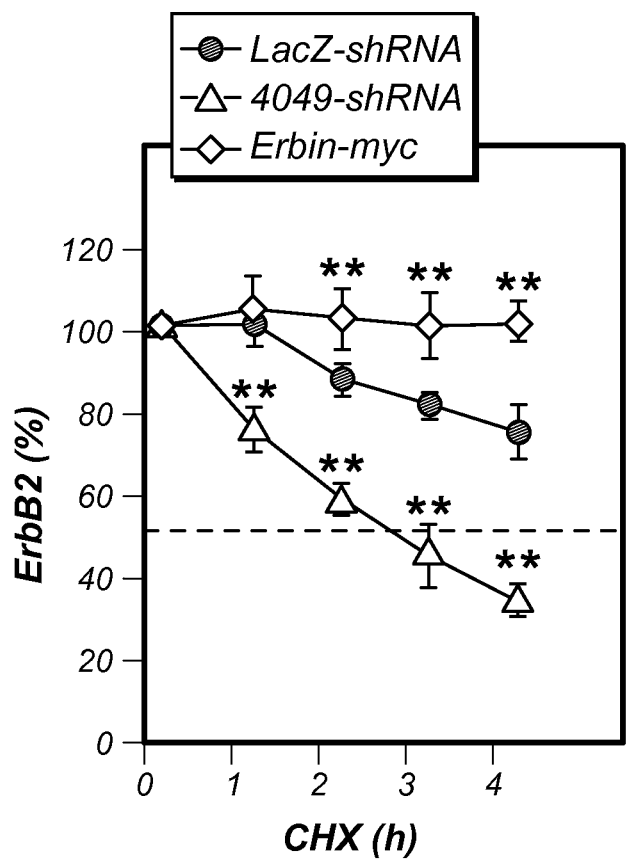
FIG. 3b is a graph showing relative expression of ErbB2 in HEK293 cells transfected with 4049-shRNA (triangles), control LacZ-shRNA (circles), or Erbin-myc (diamonds) as a function of time (hours) post-transfection. n=3;  P<0.01, compared with lacZ-shRNA-transfected cells.

HEK293 cells were then transfected with Flag-ErbB2 and shRNA constructs or Erbin-myc. Seventy-two hours after transfection, cells were cultured in a medium containing 50 mM CHX for indicated time, and lyzed. Lysates were probed for indicated proteins. Remarkably, ErbB2 degraded faster in 4049-shRNA-expressing cells in comparison with cells transfected with control lacZ-shRNA. Quantitative analysis revealed that the half-life of ErbB2 in control cells was 7.99±1.45 h (n=3), which became significantly shorter (2.70±0.374 h, n=3, P<0.01) in 4049-shRNA-transfected cells (FIG. 3b), indicating that ErbB2 was less stable in cells that express less Erbin. To test this hypothesis further, cells were transfected with Erbin, and it was found that ErbB2 became more stable in cells that overexpressed Erbin (FIG. 3b). Its levels barely changed within 4 h of experiments. The positive correlation between Erbin levels and ErbB2 stability indicate a necessary role of Erbin in maintaining ErbB2 stability.

Example 4

Mechanisms Used by Erbin to Regulate ErbB2 Stability and Internalization

Materials and Methods
Reagents.
NRG1 used is a recombinant polypeptide containing the entire EGF domain of the β-type NRG1 (rHRG β177-244) as a gift from Dr. Mark Sliwkowski (Holmes W E, et al. *Science* 256:1205-10).

Endocytosis Assays.
Surface proteins were biotinylated by 1.5 mg/mL sulfo-NHS-SS-biotin (Pierce) in DMEM at 4° C. for 60 min. After washing with cold HBSS (with $Ca^{2+}$ and $Mg^{2+}$) 3 times, cells were incubated at 37° C. for indicated times in DMEM with or without NRG1 to allow endocytosis to occur. Remained surface biotin was cleaved by incubation (15 min each, twice) with the glutathione cleavage buffer (50 mM glutathione, 75 mM NaCl, 10 mM EDTA, 1% BSA, and 0.075 N NaOH). Cells were washed with cold HBSS and lyzed with modified RIPA buffer. Cell lysates were incubated with streptavidin beads (Pierce) on a rotating platform overnight at 4° C. Precipitated biotinylated proteins were eluted by incubating the beads with 1× SDS-sample buffer and were analyzed by immunoblotting. All processes were performed with lysosome inhibitor leupeptin and proteasome inhibitor MG132.
Results
Degradation of transmembrane proteins is initiated by internalization (Yarden Y, et al. Nat Rev Mol Cell Biol. 2001 2:127-37). To explore mechanisms by which Erbin regulates ErbB2 stability, it was examined if ErbB2 internalization changes with Erbin levels. COST cells were transfected with Flag-ErbB2 and ErbB3 and LacZ-shRNA, 4049-shRNA, or Erbin-myc constructs. Seventy-two hours after transfection, cells were starved for 28 h and then incubated with sulfo-NHS-SS-biotin to label surface protein, and incubated at 37° C. for indicated time with or without NRG1 (10 nM) to allow endocytosis to occur. After cleaving surface biotin, cells were lyzed and lysates incubated with streptavidin beads to isolate internalized ErbB2, which was revealed by immunoblotting. Lysates were also probed for ErbB2 (total).

Figure 3C:
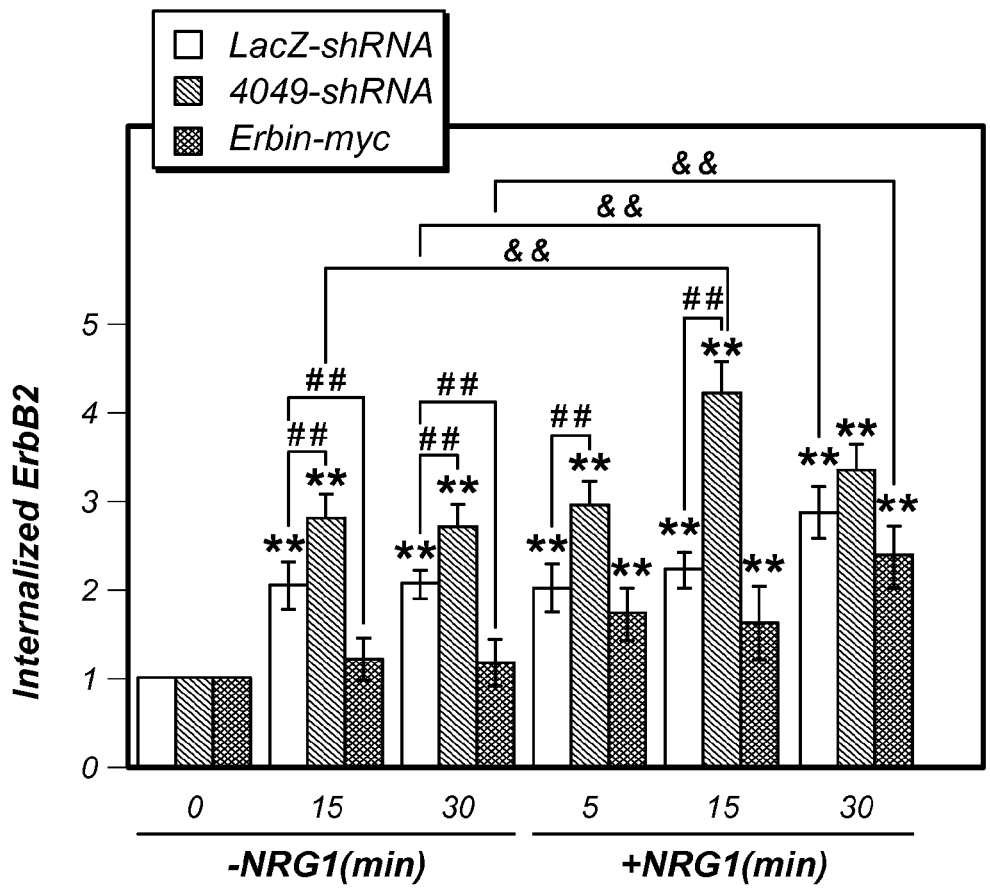
FIG. 3c is a bar graph showing internalized ErbB2 in COST cells transfected with Flag-ErbB2 and ErbB3 and 4049-shRNA (middle bars), control LacZ-shRNA (left bars), or Erbin-myc (right bars) as a function of time (min) post-transfection in medium with 10 nM NRG1 (right three sets of bars) or without NRG1 (left three sets of bars). n=3; ** P<0.01 in comparison with time 0; ##P<0.01 in comparison with lacZ-shRNA-transfected cells; && P<0.01 in comparison between cells treated with or without NRG1.

In the absence of NRG1, internalized ErbB2 was higher in 4049-shRNA-transfected cells in comparison with that in lacZ-shRNA-transfected cells (FIG. 3c). In contrast, less ErbB2 was internalized in cells overexpressing Erbin (FIG. 3c). These results indicate Erbin can regulate constitutive ErbB2 internalization. To investigate whether Erbin also regulates NRG1-induced ErbB2 endocytosis, cells were stimulated by NRG1 for 0, 15 or 30 minutes before biotin cleavage. In agreement with previous reports (Yang X L, et al. *Mol Cell Neurosci.* 2005 28:335-46), NRG1 stimulated ErbB2 internalization (FIG. 3c). Intriguingly, NRG1-induced ErbB2 internalization was accelerated and enhanced in 4049-shRNA-transfected cells in comparison with that in control cells (FIG. 3c). The amounts of NRG1-induced endocytosed ErbB2 in Erbin-overexpressing cells appeared to be less than those in control cells although no statistical significance was observed in quantitative analysis. These results suggest that the level of Erbin regulates both constitutive and NRG1-stimulated ErbB2 internalization.

Example 5

Materials and Methods
Reagents.
Antibodies (with catalog number) used are from Cell signaling Technology (pAkt, 9271; Akt, 9272), Upstate (4G10, 16-105),
Schwann Cell Culture.
Primary Schwann cells were prepared by a modified protocol (Taveggia C, et al. Neuron 47:681-94; Weinstein D E, et al. *Curr Protoc Neurosci Chapter* 3, Unit 3 17). Briefly, rat sciatic nerves were digested in 3 mg/mL collagenase at 37° C. for 30 min, and incubated with 0.25% trypsin at 37° C. for 5 min. Digested nerves were passed through 18-G needles (15 times) and 20-G needles (7 times). Dissociated cells were isolated by centrifuging for 5 min at 150 g. Cell pellets were resuspended in DMEM/10% FBS and plated onto PLL-coated 100 mm dishes. AraC (5 μM) was added into media the next day for 72 h to suppress the growth of fibroblasts. Confluent cells were dissociated by trypsin digestion and subjected to immunopanning with Thy1.1 to eliminate fibroblasts. After replating, cells were cultured in media supplemented with 2 μM forskolin and 10 μg/mL insulin instead of NRG1, to avoid interfering ErbB signaling. More than 98% purity of SC cells, assayed by the SC specific marker S100, was obtained.

Nucleofection.

Transfection was performed by nucleofection using Nucleofector II (Amaxa) per manufacture's instructions. In brief, 4-5 μg plasmids were nucleofected into 2-4×10$^6$ cells by using program Q-001 for HEK293, A-024 for COS7 and T-030 for rat SCs (Haastert K, et al. *Nat Protoc* 2:99-104). Nucleofected SCs were plated on 6-well plates precoated with PLL and laminin. More than 90% transfection efficiency was routinely achieved in primary SCs. Cells were used for experiments 72 h after plating to allow knockdown of Erbin. Cells were starved in DMEM/1% FBS for 24 h and DMEM without serum for 4 h before NRG1 stimulation.

Immunoprecipitation.

SC lysates were cleaned by centrifugation at 16,000×g for 15 min and were subjected to immunoprecipitation with polyclonal antibody against ErbB3 at 4° C. for overnight and protein-A agarose (Roche, Germany) at room temperature for 1 h. Bound proteins were resolved by SDS/PAGE and analyzed by immunoblotting with monoclonal antibody recognizing phosphotyrosine (4G10). Blots were reprobed with ErbB3 antibody to check immunoprecipitating efficiency.

Results

NRG1 activates various intracellular pathways including PI3K/Akt, MAPK, and JNK (Mei L, et al. *Nat Rev Neurosci.* 2008 9:437-52). Among them, the PI3K/Akt pathway appears to be a major effecter of NRG1 to regulate myelination (Flores A I, et al. *J Neurosci.* 2008 28:7174-83). Having demonstrated that Erbin regulates ErbB2 stability and internalization, it was next tested if Erbin deficiency alters intracellular signaling by NRG1.

Figure 7A:
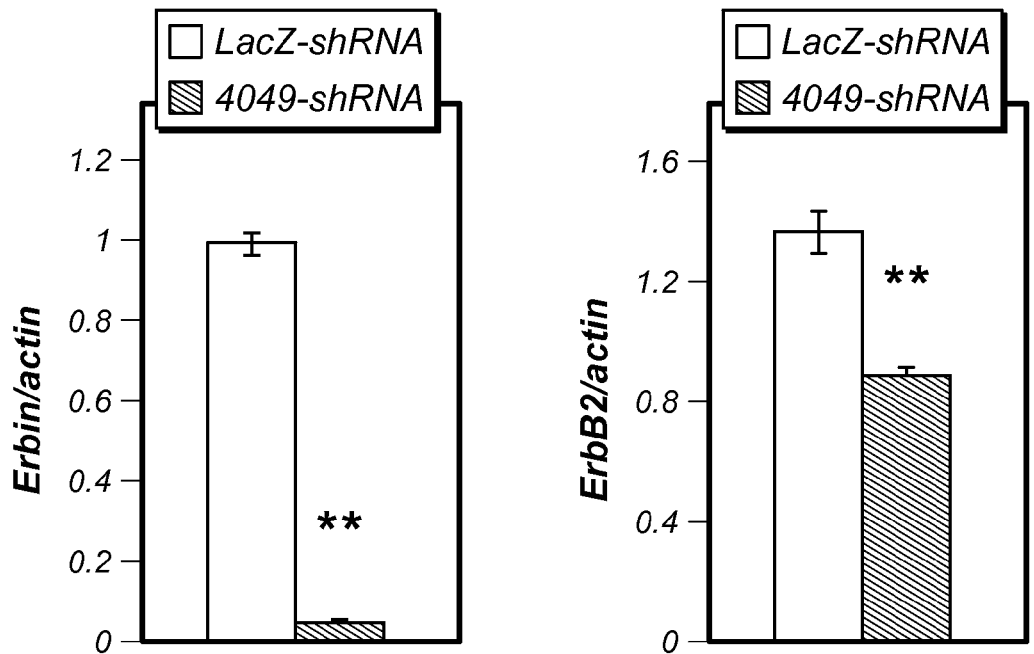
FIG. 7a is a set of bar graphs showing relative expression of Erbin (left graph) and ErbB2 (right graph) normalized to β-actin in primary SCs transfected with lacZ-shRNA (left bars) or 4049-shNRA (right bars). n=3; ** P<0.01.

Primary Schwann cells were transfected with control shRNA or 4049-shRNA, which suppressed Erbin expression in SCs (FIG. 7a). Specifically, SCs were transfected by nucleofection with LacZ-shRNA or 4049-shRNA and analyzed for expression of Erbin, ErbB2, ErbB3, and β-actin 72 h after transfection. Note that the experiment was done in the absence of NRG.

Figure 3D:
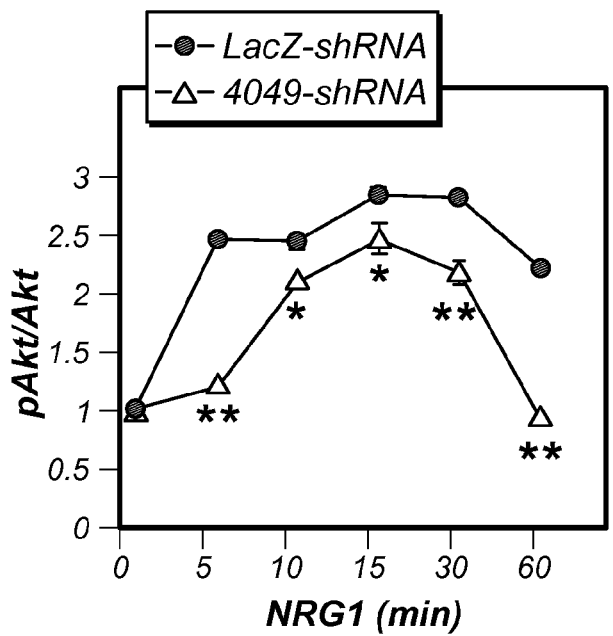
FIG. 3d is a graph showing relative expression of pAkt/Akt in primary SCs transfected with 4049-shRNA (triangles) or control LacZ-shRNA (circles) as a function of time (min) post-transfection in medium with 5 nM NRG1. n=3; * P<0.05;  P<0.01 in comparison with cells transfected with lacZ-shRNA.

Akt activation was assayed by specific antibody against active Akt. Specifically, transfected primary SCs were starved for 28 h and then stimulated with or without NRG1 (5 nM), and probed for active Akt (pAkt) by immunoblotting. Total Akt and β-actin were also blotted to indicate equal amounts of proteins. Expression of any of the constructs had no effect on Akt levels (FIG. 3d). In cells transfected with control shRNA, NRG1 elicited rapid activation of Akt, which remained at high levels 60 min after stimulation. In contrast, suppression of Erbin expression inhibited Akt activation by NRG1, which was delayed and more transient, returning to basal level within 60 min of stimulation. The altered kinetics of Akt activity and ErbB2 endocytosis indicate that Erbin controls the time and amplitude of NRG1 signaling.

Figure 3E:
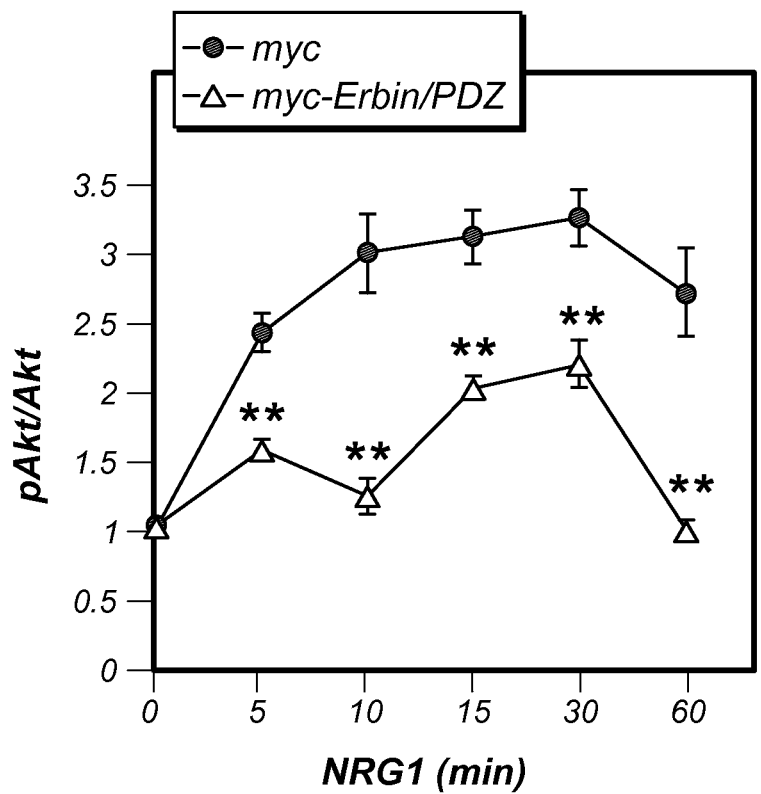
FIG. 3e is a graph showing relative expression of pAkt/Akt in primary SCs transfected with myc vehicle vector (circles) or myc-Erbin/PDZ (triangles) as a function of time (min) post-transfection in medium with 5 nM NRG1. n=3; , P<0.01 in comparison with cells transfected with vehicle vector (myc).

To eliminate the possibility of off-target effect of 4049-shRNA, the PDZ domain of Erbin (myc-Erbin/PDZ), which functions in a dominant negative manner to prevent ErbB2 from interacting with endogenous Erbin, was overexpressed. Expression of the PDZ domain had similar effect on Akt activation to that by shRNA. The similar effects by these 2 different approaches (dominant negative inhibition and shRNA knockdown) provide strong evidence that Erbin regulates NRG1 signaling in SCs (FIG. 3e).

Figure 7B:
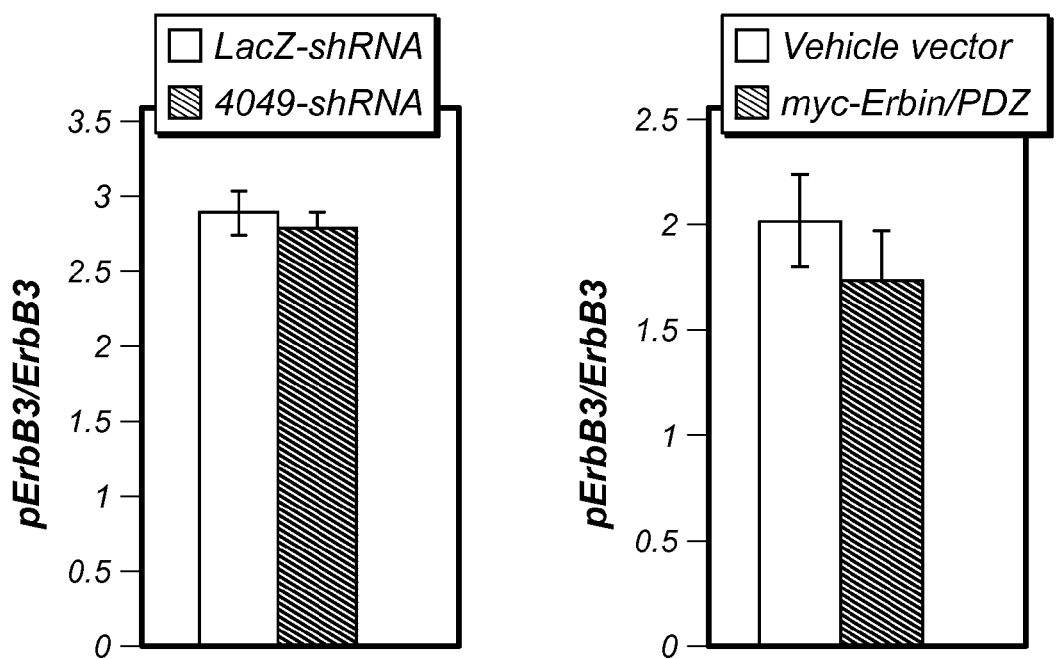
FIG. 7b is a set of bar graphs showing the relative amount of phosphorylated ErbB3 (pErbB3) normalized to total ErbB3 in primary SCs transfected with lacZ-shRNA (left graph, left bar), 4049-shNRA (left graph, right bar), myc vehicle vector (right graph, left bar) or myc-Erbin/PDZ (right graph, right bar). n=3.

Lysates of control or NRG1 (10 min)-treated cells were subjected to immunoprecipitation and blotting with antibodies to pTyr, ErbB3, ErbB2, and β-actin. Note that expression of 4049-shRNA and PDZ did not appear to alter NRG1-induced ErbB phosphorylation (FIG. 7b), indicating that Erbin acts by stabilizing surface ErbB proteins.

Figure 3F:
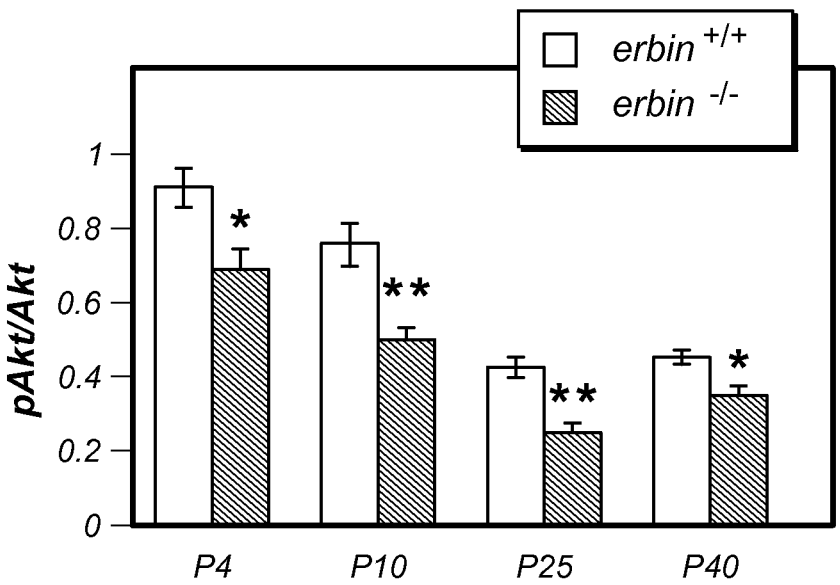
FIG. 3f is a bar graph showing relative expression of pAkt/Akt in sciatic nerves of erbin$^{-/-}$ mice (right bars) or erbin$^{+/+}$ mice (left bars) as a function of postnatal stage (P4, P10, P25, P40). n=3; * P<0.05; ** P<0.01.

To determine whether Akt activation is altered in erbin$^{-/-}$ mice, active Akt was measured in sciatic nerves of erbin$^{-/-}$ and control mice. Specifically, sciatic nerves from erbin$^{+/+}$ and erbin$^{-/-}$ littermate mice at different ages were homogenized, and homogenates were subject to SDS/PAGE and probed for pAkt. Total Akt and β-actin were also probed to indicate equal amounts of proteins. Significantly, phospho-Akt was consistently lower in erbin$^{-/-}$ sciatic nerves than that in control littermates during development (FIG. 3f). Together, these observations indicate a critical role of Erbin in NRG1 activation of PI3K/Akt in SCs.

Example 6

Materials and Methods

Reagents.

Antibodies (with catalog number) used are from Abcam (Thy1.1, ab50200), and Santa Cruz Biotechnology (P0, sc-18531;

Results

If Erbin regulation of myelination depends on maintaining ErbB2 stability and NRG1 signaling, in vivo deletion of the PDZ domain that interacts with ErbB2 should duplicate the phenotypes of erbin$^{-/-}$ mice. To this end, erbin$^{\Delta C/\Delta C}$ mice that were generated by gene trapping (FIGS. 4a-f) were characterized.

Figure 8A:
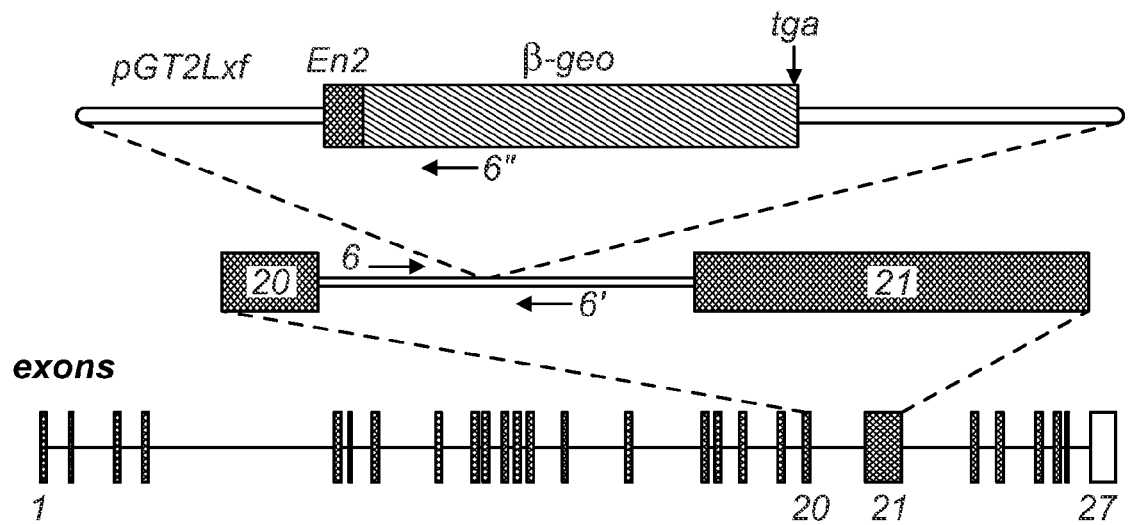
FIG. 8a is a schematic diagram illustrating the genetrap vector used to generate erbin$^{\Delta C/\Delta C}$ mice. pGT2Lxf was insertion between exons 20 and 21. pGT2Lxf contains En2, the splice acceptor/Engrailed-2 exon and β-geo. Arrows indicate the orientation of genotyping primers 6, 6' and 6".
Figure 8B:
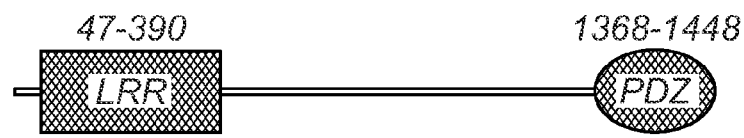
FIG. 8b is a schematic diagram illustrating the Domain structures of Erbin and Erbin$_{1-693}$βgal proteins. Mutant Erbin contains the N-terminal 693 aa residues, which are fused in frame with 6 amino acid residues encoded by En2 and β-gal and is thus named Erbin$_{1-693}$βgal.
Figure 8B:

Erbin in erbin$^{\Delta C/\Delta C}$ mice was replaced by a mutant protein with C-terminal truncation (Erbin$_{1-693}$βgal). Specifically, the β-gal gene (β-geo) was inserted downstream of exon 20 of the erbin gene, producing a chimerical mRNA of erbin and β-geo mRNAs. The mRNA encodes a fusion protein containing the N-terminal 693 aa residues and β-gal (thus named as Erbin$_{1-693}$ βgal). FIG. 8a is a schematic diagram of the genetrap vector pGT2Lxf insertion between exons 20 and 21. pGT2Lxf contains En2, the splice acceptor/Engrailed-2 exon and β-geo. PCR products were generated by primers 6 and 6' on intro 20 for wt, but not mutant (mt) allele; and by primers 6 and 6" on β-geo for mt, but not wt, allele. Total RNA was isolated from Erbin mutant mouse brain and resulting cDNA was used as template in PCR with primers P20 and β-geo. No PCR product was generated by this pair of primers for wt cDNA. The mutation generates a chimerical mRNA of exons 1-20 of erbin at 5'-end and β-geo at 3'-end. DNA sequencing revealed that the truncated Erbin and β-gal are in the same reading frame, but the mutant fusion protein contains extra 6 aa residues. Mutant Erbin contains the N-terminal 693 aa residues, which are fused in frame with 6 amino acid residues encoded by En2 and β-gal and is thus named Erbin$_{1-693}$βgal (FIG. 8b). Immunoblot analyses revealed gene-dosage-dependent expression of Erbin$_{1-693}$βgal at predicted 210 kDa. Brain homogenates were subjected to immunoblotting with antibody against the PDZ domain of Erbin or anti-βgal antibody. Erbin expression was reduced in erbin$^{+/\Delta C}$ (+/ΔC) and ablated in erbin$^{\Delta C/\Delta C}$ (ΔC/ΔC) samples whereas Erbin$_{1-693}$βgal was not detectable in erbin$^{+/+}$ (+/+) but in erbin$^{+/\Delta C}$ and erbin$^{\Delta C/\Delta C}$ samples.

Figure 4A:
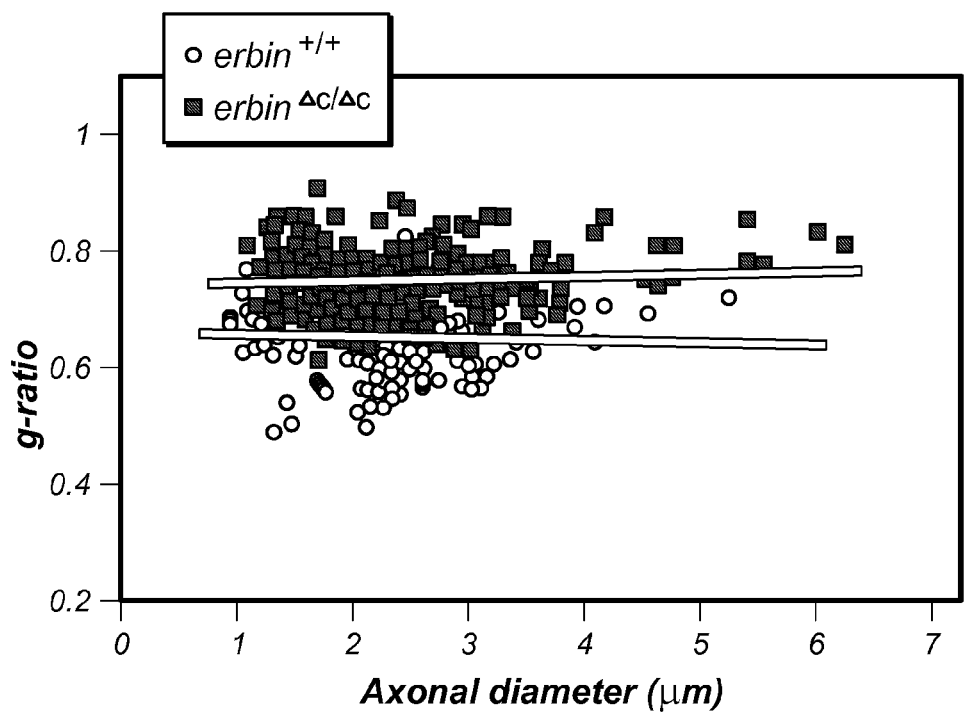
FIG. 4a is a graph showing g-ratio as a function of axonal diameter ($\mu m$) in erbin$^{+/+}$ (circles) and erbin$^{\Delta C/\Delta C}$ (squares) mice.
Figure 4B:
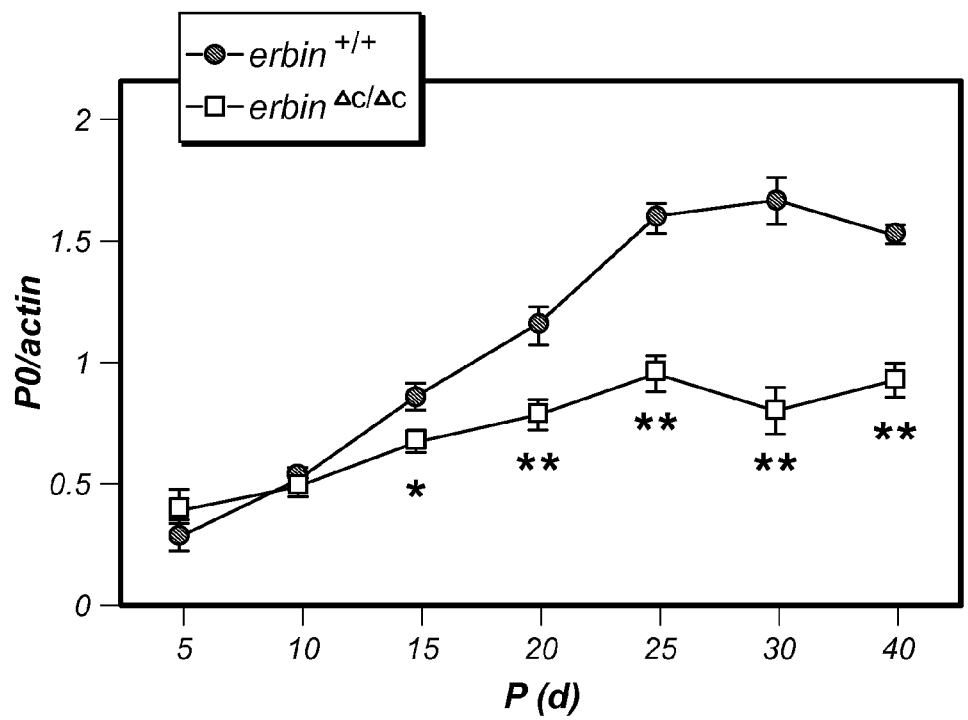
FIG. 4b is a graph showing relative Myelin protein zero (P0) expression normalized to β-actin as a function of postnatal stage (P7, P15, P25, P40) in erbin$^{+/+}$ (circles) and erbin$^{\Delta C/\Delta C}$ (squares) mice. n=3, * P<0.05,  P<0.01.
Figure 4C:
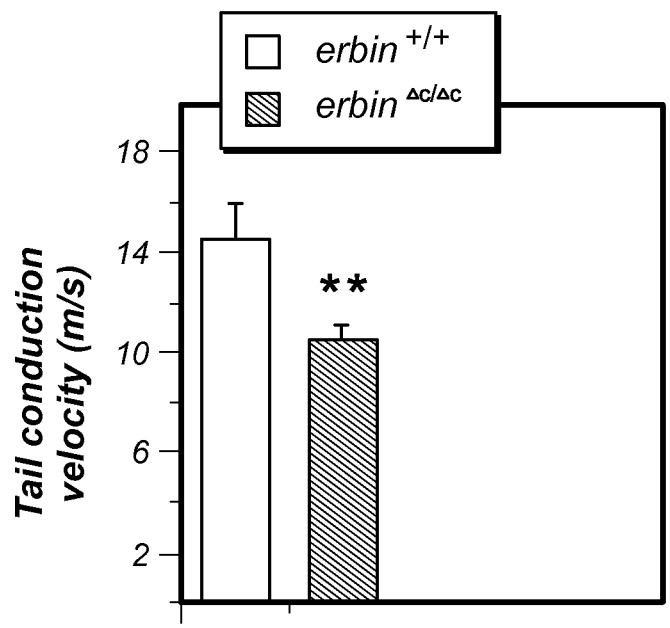
FIG. 4c is a bar graph showing tail conduction velocity (m/s) in erbin$^{+/+}$ (left bar) and erbin$^{\Delta C/\Delta C}$ (right bar) mice. n=4,  P<0.01.
Figure 4D:
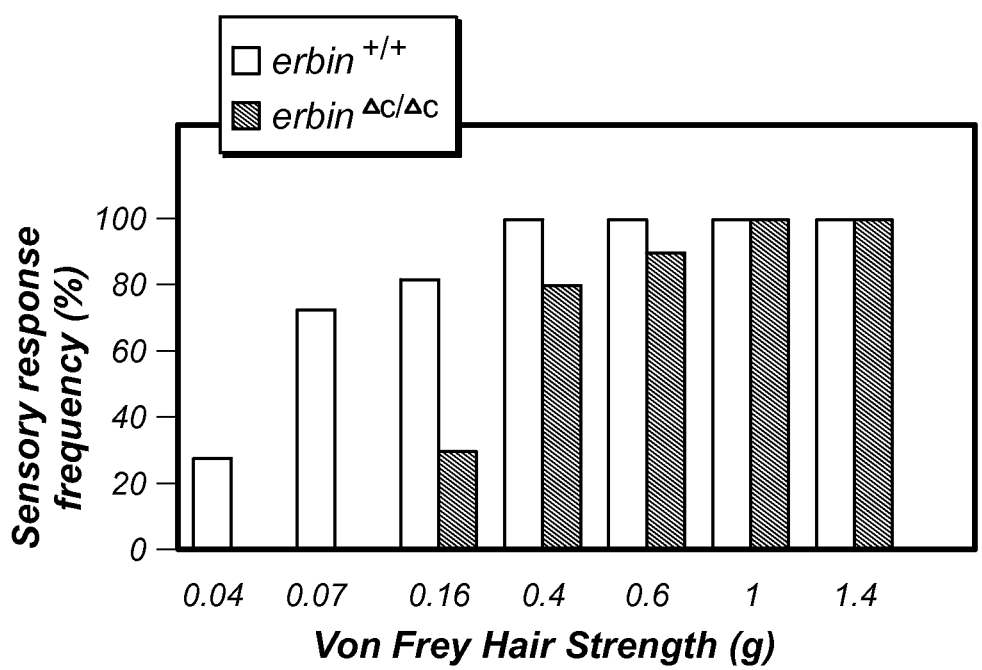
FIG. 4d is a bar graph showing percentages of mice responding to Von Frey Hair stimulation as a function of Von Frey Hair Stregth (g) for erbin$^{+/-}$ (left bars) and erbin$^{\Delta C/\Delta C}$ (right bars) mice. n=8 mice in each group.
Figure 4E:
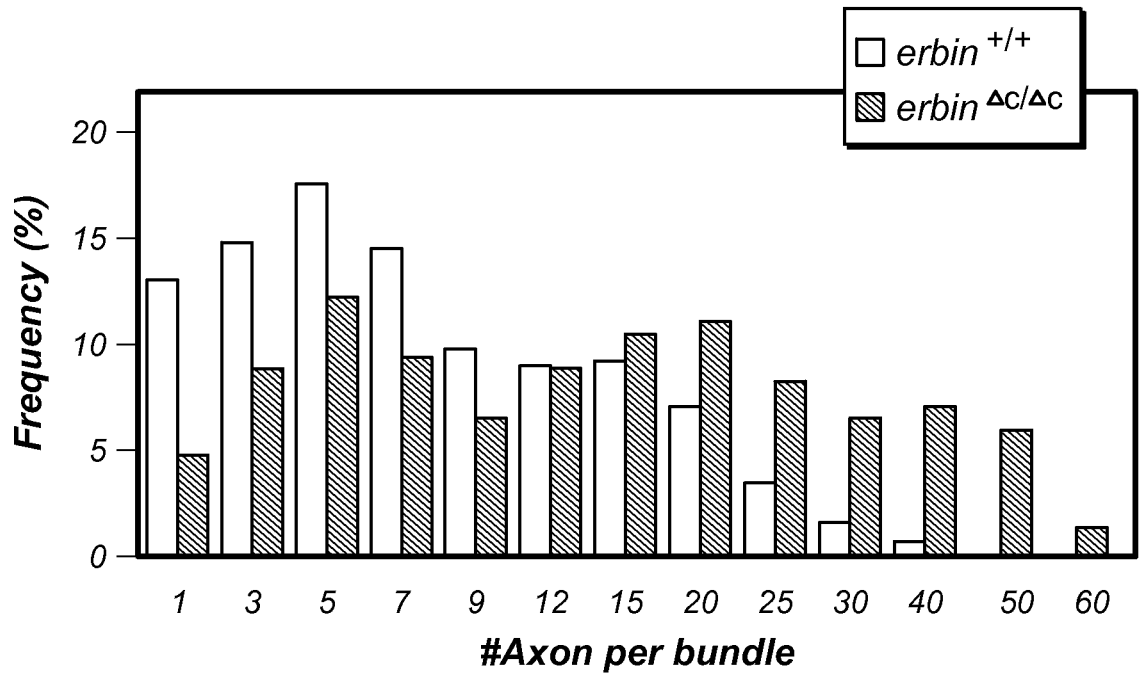
FIG. 4e is a bar graph showing the frequency (percentage) of mice as a function of the number of unmyelinated axons in Remak bundles in erbin$^{+/+}$ (left bars) and erbin$^{\Delta C/\Delta C}$ (right bars) sciatic nerves. Remak bundles analyzed were 359 for erbin$^{+/+}$ and 272 for erbin$^{\Delta C/\Delta C}$.
Figure 4F:
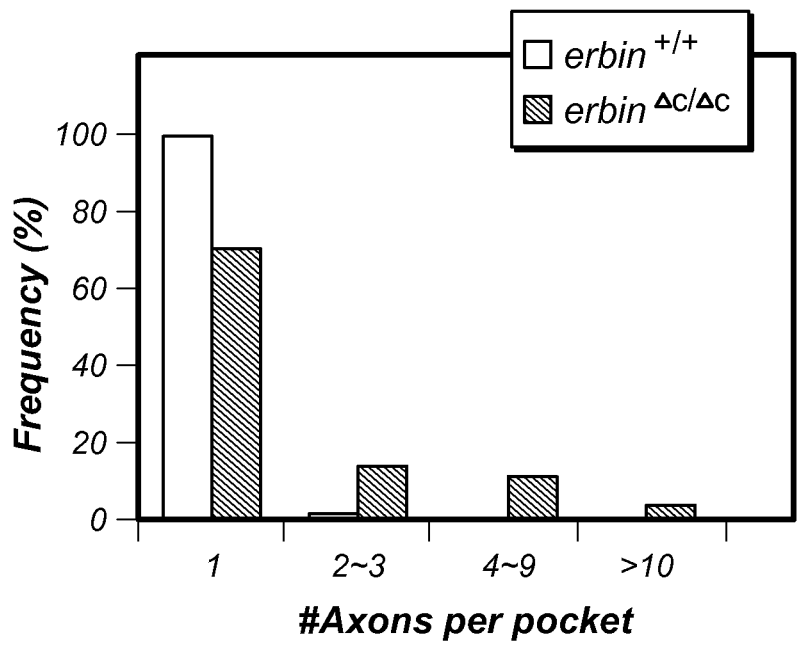
FIG. 4f is a bar graph showing the frequency (percentage) of mice as a function of the number of unmyelinated axons in SC pockets in erbin$^{+/+}$ (left bars) and erbin$^{\Delta C/\Delta C}$ (right bars) sciatic nerves. Pockets analyzed were 2852 for erbin$^{+/+}$ and 1988 for erbin$^{\Delta C/\Delta C}$.
Figure 4G:
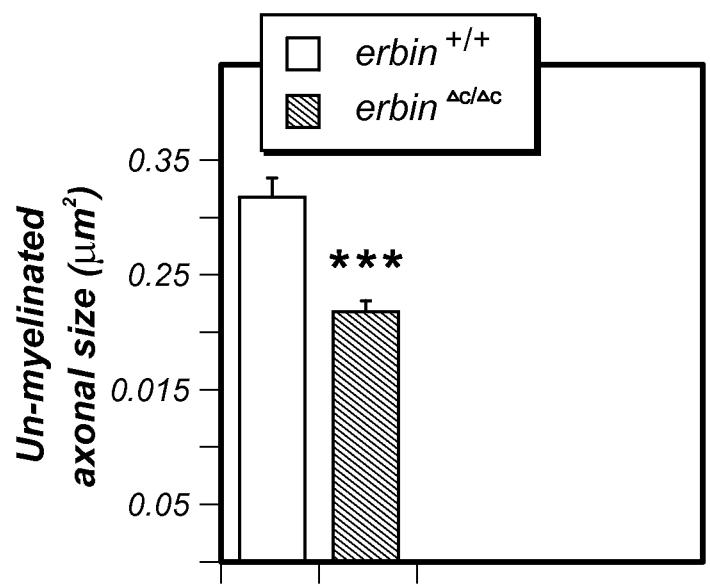
FIG. 4g is a bar graph showing the unmyelinated axonal size ($\mu m^2$) in erbin$^{+/+}$ (left bar) and erbin$^{\Delta C/\Delta C}$ (right bar) sciatic nerves. n=97 for erbin$^{+/+}$, n=102 for erbin$^{\Delta C/\Delta C}$, *** P<0.001. The age of mice was P30 in A, B, and G-J and P60 in E and F.

Remarkably, erbin$^{\Delta C/\Delta C}$ mice showed similar myelin deficits of erbin$^{-/-}$ mice. First, myelinated axons had thinner myelin without apparent changes in ultrastructure and periodicity. Averaged g-ratio of myelinated axons increased from 0.644±0.0196 (n=169) in wild-type to 0.738±0.0134 (n=277, P<0.001) in erbin$^{\Delta C/\Delta C}$ mice, regardless of axonal size (FIG. 4a). P0 protein levels were lower in erbin$^{\Delta C/\Delta C}$ sciatic nerves than those in littermates (FIG. 4b). Functionally, erbin$^{\Delta C/\Delta C}$ mice had reduced nerve conduction velocity (FIG. 4c) and elevated mechanical sensory threshold (FIG. 4d). Second, similar deficits were observed in unmyelinated fibers. Remak bundles in erbin$^{\Delta C/\Delta C}$ mice contained more unmyelinated axons. Quantitative analyses indicate a substantial increase in the number of bundles containing 20 or more axons (FIG. 4e). Axons in Remak bundles were segregated completely and smaller in size (FIG. 4g), resulting increased number of axons in SC pockets (FIG. 4f). These observations demonstrate similar deficits in myelination and ensheathment of sciatic nerves in erbin$^{-/-}$ and erbin$^{\Delta C/\Delta C}$ mice. The phenotypic similarity provides strong genetic evidence that the null mutation and C-terminal truncation share mechanism of action and indicates a critical role of the PDZ domain of Erbin in regulation of myelination.

Figure 9A:
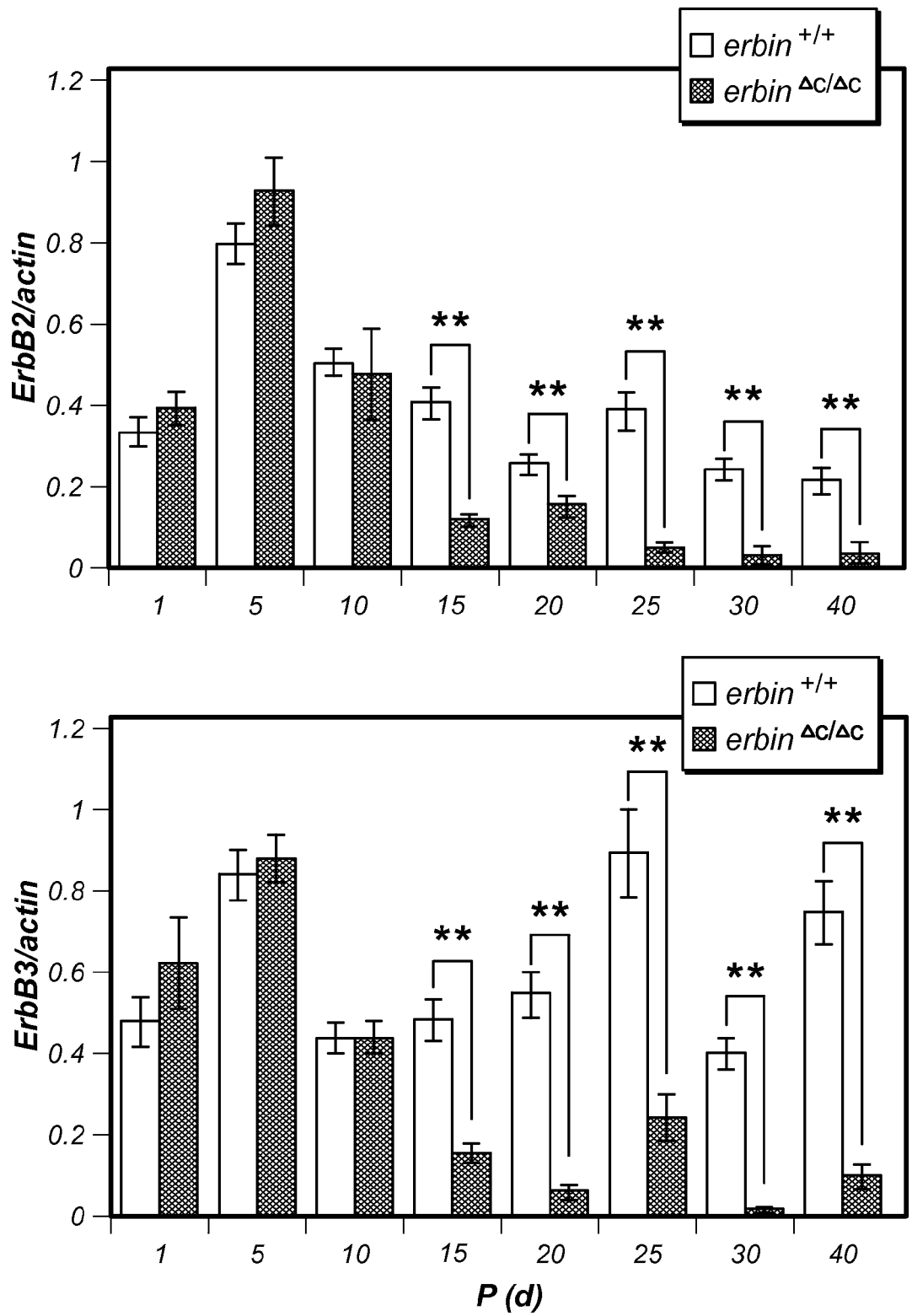
FIG. 9a is a set of bar graphs showing relative expression of ErbB2 (top graph) and ErbB3 (bottom graph) normalized to β-actin as a function of postnatal stage (P1, P5, P15, P20, P25, P30, P40) in erbin$^{+/+}$ (left bars) and erbin$^{\Delta C/\Delta C}$ (right bars) sciatic nerves.
Figure 9B:
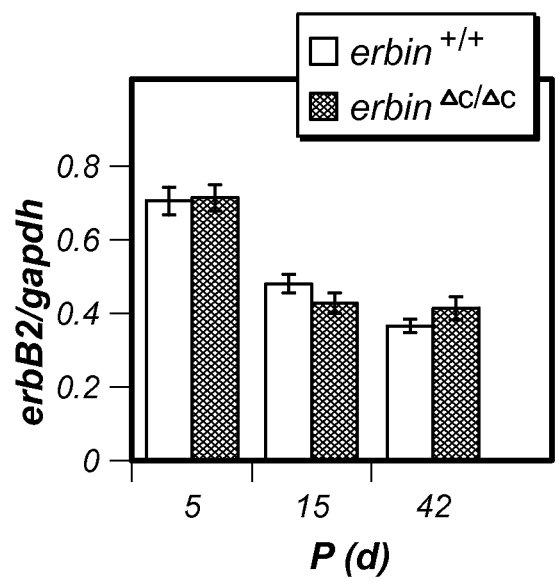
FIG. 9b is a bar graph showing relative expression of ErbB2 mRNA normalized to gapdh as a function of postnatal stage (P5, P15, P42) in erbin$^{+/+}$ (left bars) and erbin$^{\Delta C/\Delta C}$ (right bars) sciatic nerves.
Figure 9C:
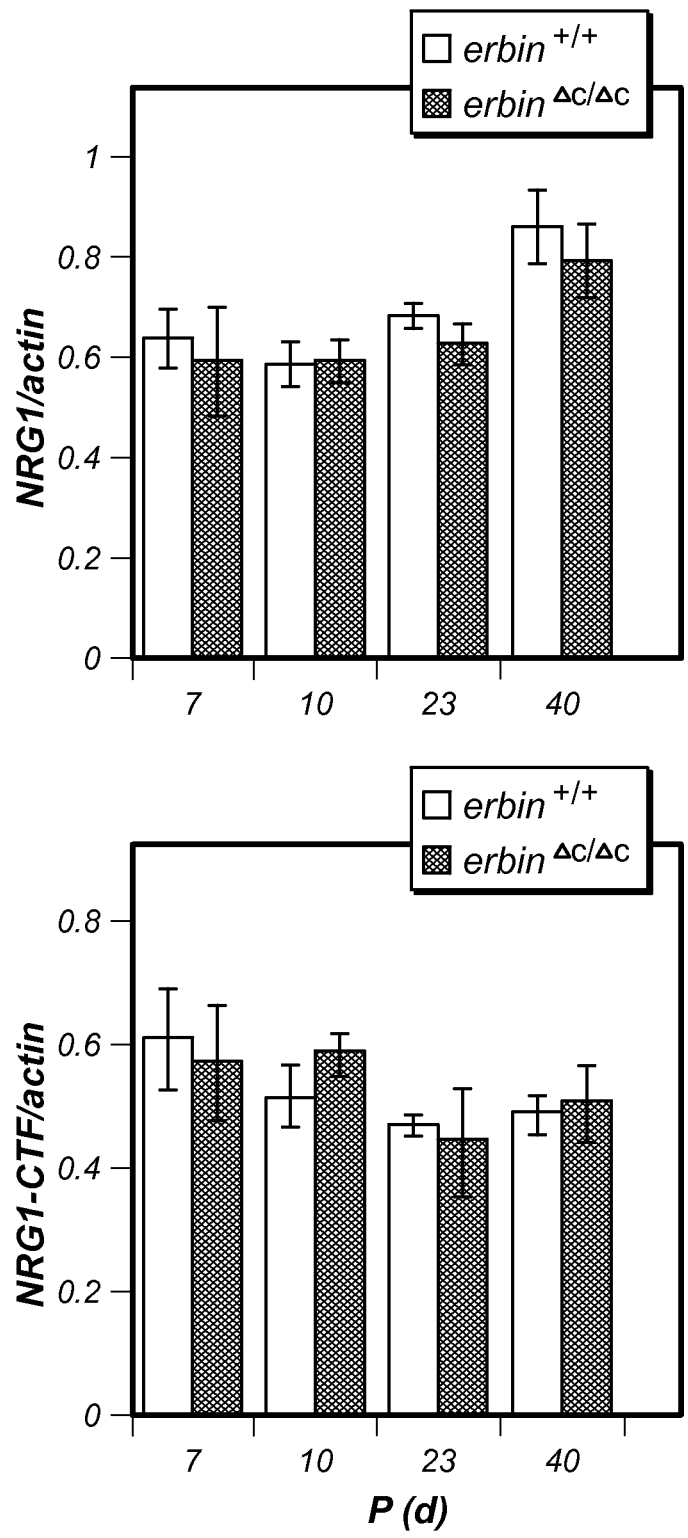
FIG. 9c is a set of bar graphs showing relative expression of neuregulin 1 (NRG1, top graph) and its C-terminal fragment (NRG1-CTF, bottom graph) normalized to β-actin as a function of postnatal stage (P7, P10, P23, P40) in erbin$^{+/+}$ (left bars) and erbin$^{\Delta C/\Delta C}$ (right bars) sciatic nerves. n=3.

This idea is supported by biochemical studies that ErbB receptors were reduced at protein (FIG. 9a), but not mRNA, levels (FIG. 9b) in erbin$^{\Delta C/\Delta C}$ sciatic nerves. Note that NRG1 levels were similar in mutant mice (FIG. 9c).

These observations suggest unique NRG1 signaling mechanisms in oligodendrocyte-dependent myelination. However, CNS myelination were apparently normal in erbin$^{-/-}$ and erbin$^{\Delta C/\Delta C}$ mice. EM images of optic nerve cross-sections from P30 mice were shown at 2 different magnifications. Similar myelin in erbin$^{-/-}$ and control optic nerves was observed. Also observed was overlapped distribution of g-ratio in erbin$^{-/-}$ and control optic nerves. Likewise, similar MBP levels were observed in erbin$^{-/-}$ and control corpus callosum and medulla. There was also similar MBP staining in corpus callosum of erbin$^{-/-}$ and control mice. There was also similar myelin in erbin$^{\Delta C/\Delta C}$ and control optic nerves. There was also overlapped distribution of g-ratio in erbin$^{\Delta C/\Delta C}$ and control optic nerves. There was also similar MBP levels in erbin$^{\Delta C/\Delta C}$ and control corpus callosum and medulla. Thus, there were no consistent changes were observed in optical nerve myelination and levels of MBP, a key CNS myelin protein, in erbin$^{-/-}$ and erbin$^{\Delta C/\Delta C}$ mice, suggesting that Erbin is specifically involved in PNS, but not CNS, myelination.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of inhibiting ErbB2 activity in cells, comprising contacting the cell with a composition comprising an Erbin antagonist, wherein the Erbin antagonist is a polypeptide fragment of Erbin selected from the group consisting of a polypeptide consisting of amino acids 1307 to 1366 of SEQ ID NO:1 and a polypeptide consisting of amino acids 694 to 1371 of SEQ ID NO:1.

2. The method of claim 1, wherein the polypeptide fragment of Erbin binds ErbB2 under physiological conditions.

3. The method of claim 1, wherein the Erbin antagonist inhibits Erbin binding to ErbB2 under physiological conditions.

4. A method of treating a cancer in a subject, wherein the cancer is characterized by ErbB2 overexpression, comprising administering to the subject a pharmaceutical composition comprising an Erbin antagonist in a pharmaceutically acceptable excipient, wherein the Erbin antagonist is a polypeptide fragment of Erbin selected from the group consisting of a polypeptide consisting of amino acids 1307 to 1366 of SEQ ID NO:1 and a polypeptide consisting of amino acids 694 to 1371 of SEQ ID NO:1.

5. The method of claim 4, wherein the polypeptide fragment of Erbin binds ErbB2 under physiological conditions.

6. The method of claim 4, wherein the Erbin antagonist causes inhibition of ErbB2 activity.

* * * * *